US010881137B2

(12) United States Patent
Suzuki et al.

(10) Patent No.: US 10,881,137 B2
(45) Date of Patent: Jan. 5, 2021

(54) FLAVOR INHALER

(71) Applicant: JAPAN TOBACCO INC., Tokyo (JP)

(72) Inventors: Akihiko Suzuki, Tokyo (JP); Manabu Takeuchi, Tokyo (JP); Takuma Nakano, Tokyo (JP); Manabu Yamada, Tokyo (JP)

(73) Assignee: JAPAN TOBACCO INC., Tokyo (JP)

(*) Notice: Subject to any disclaimer, the term of this patent is extended or adjusted under 35 U.S.C. 154(b) by 335 days.

(21) Appl. No.: 15/712,705

(22) Filed: Sep. 22, 2017

(65) Prior Publication Data

US 2018/0007960 A1 Jan. 11, 2018

Related U.S. Application Data

(63) Continuation of application No. PCT/JP2016/060251, filed on Mar. 29, 2016.

(30) Foreign Application Priority Data

Apr. 2, 2015 (WO) .................. PCT/JP2015/060493

(51) Int. Cl.
*A24F 47/00* (2020.01)
*A61M 15/06* (2006.01)
*A61M 15/00* (2006.01)

(52) U.S. Cl.
CPC ............ *A24F 47/006* (2013.01); *A24F 47/00* (2013.01); *A24F 47/008* (2013.01); *A61M 15/06* (2013.01); *A61M 15/0021* (2014.02); *A61M 2205/3331* (2013.01)

(58) Field of Classification Search
None
See application file for complete search history.

(56) References Cited

U.S. PATENT DOCUMENTS

| 4,936,920 | A | * | 6/1990 | Keritsis | .................... | A24C 5/18 |
| | | | | | | 131/352 |
| 5,095,921 | A | | 3/1992 | Losee et al. | | |
| 5,479,948 | A | | 1/1996 | Counts et al. | | |

(Continued)

FOREIGN PATENT DOCUMENTS

| CA | 2420623 A1 | 2/1995 |
| EP | 0 845 220 A1 | 6/1998 |

(Continued)

OTHER PUBLICATIONS

Australian Office Action for Australian Application No. 2016240554, dated Sep. 7, 2018.

(Continued)

*Primary Examiner* — Michael H. Wilson
*Assistant Examiner* — Katherine A Will
(74) *Attorney, Agent, or Firm* — Birch, Stewart, Kolasch & Birch, LLP

(57) ABSTRACT

This flavor inhaler is provided with a housing having an air flow path that spans continuously from an inlet to an outlet, and an atomizing part for atomizing an aerosol source without accompanying combustion of the aerosol source, wherein at least one portion of the air flow path is an aerosol flow path which is a flow path for an aerosol generated from the atomizing part, and the air blow resistance of the whole air flow path is not greater than 25 mmAq.

19 Claims, 18 Drawing Sheets

(56) References Cited

U.S. PATENT DOCUMENTS

| | | |
|---|---|---|
| 9,854,839 B2 | 1/2018 | Tucker et al. |
| 2009/0241949 A1 | 10/2009 | Smutney et al. |
| 2011/0226236 A1 | 9/2011 | Buchberger |
| 2013/0037041 A1* | 2/2013 | Worm .................. A24F 47/008 131/329 |
| 2014/0338686 A1 | 11/2014 | Plojoux et al. |
| 2014/0353856 A1 | 12/2014 | Dubief |
| 2018/0028993 A1* | 2/2018 | Dubief .................. A24D 3/041 |
| 2018/0184721 A1 | 7/2018 | Hon |

FOREIGN PATENT DOCUMENTS

| | | |
|---|---|---|
| EP | 0845220 A1 | 6/1998 |
| EP | 3275321 A1 | 1/2018 |
| GB | 873410 A | 7/1961 |
| JP | 6-315366 A | 11/1994 |
| JP | 7-147965 A | 6/1995 |
| JP | 11-89551 A | 4/1999 |
| JP | 2009-537120 A | 10/2009 |
| JP | 2012-506263 A | 3/2012 |
| JP | 2015-500026 A | 1/2015 |
| JP | 2015-504667 A | 2/2015 |
| KR | 10-0264617 B1 | 9/2000 |
| KR | 10-2010-0134700 A | 12/2010 |
| KR | 10-2014-0110848 A | 9/2014 |
| KR | 10-2015-0005514 A | 1/2015 |
| WO | WO 97/48293 A1 | 12/1997 |
| WO | WO 2013/116558 A1 | 8/2013 |
| WO | WO 2014/045025 A2 | 3/2014 |
| WO | WO 2014/060269 A1 | 4/2014 |
| WO | WO 2014/085719 A1 | 6/2014 |
| WO | WO 2014/110119 A1 | 7/2014 |
| WO | WO 2014/130772 A1 | 8/2014 |
| WO | WO 2014/156537 A1 | 10/2014 |

OTHER PUBLICATIONS

Korean Office Action for Korean Application No. 10-2017-7029447, dated Oct. 10, 2018, with English translation.
Canadian Examination Report, dated Jul. 23, 2018, for Canadian Application No. 2,980,426.
Japanese Office Action, dated Jun. 19, 2018, for Japanese Application No. 2017-510059, with an English machine translation.
European Third Party Observation for European Application No. 16772894.8, dated Feb. 15, 2019.
Extended European Search Report dated Nov. 13, 2018, for corresponding European Patent Application No. 16772894.8.
International Search Report (PCT/ISA/210) issued in PCT/JP2016/060251, dated Jul. 5, 2016.
Written Opinion of the International Searching Authority (PCT/ISA/237) issued in PCT/JP2016/060251, dated Jul. 5, 2016.
Chinese Office Action, dated Jun. 13, 2019, for Chinese Application No. 201680019012.6, along with an English translation of the Chinese Office Action.
Eurasian Office Action, dated Aug. 15, 2019, for Eurasian Application No. 201792196, along with an English translation.
Japanese Notice of Reasons for Refusal dated Jan. 31, 2019, for Japanese Patent Application No. 2017-510059, with English translation.
Japanese Office Action, dated Aug. 28, 2019, for Japanese Application No. 2017-510059, along with an English translation.

* cited by examiner

NON-MOUTHPIECE SIDE ←——A——→ MOUTHPIECE SIDE

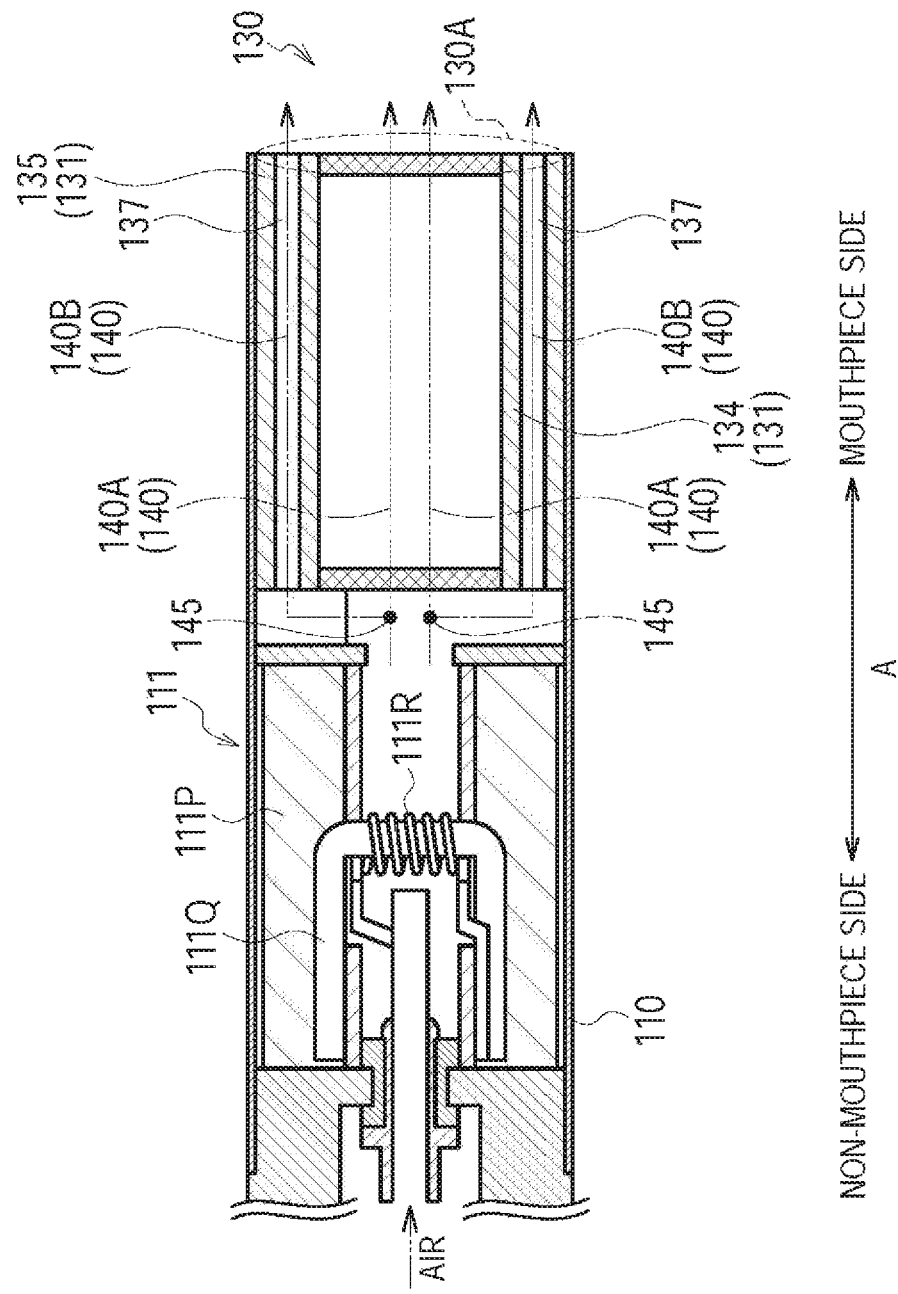

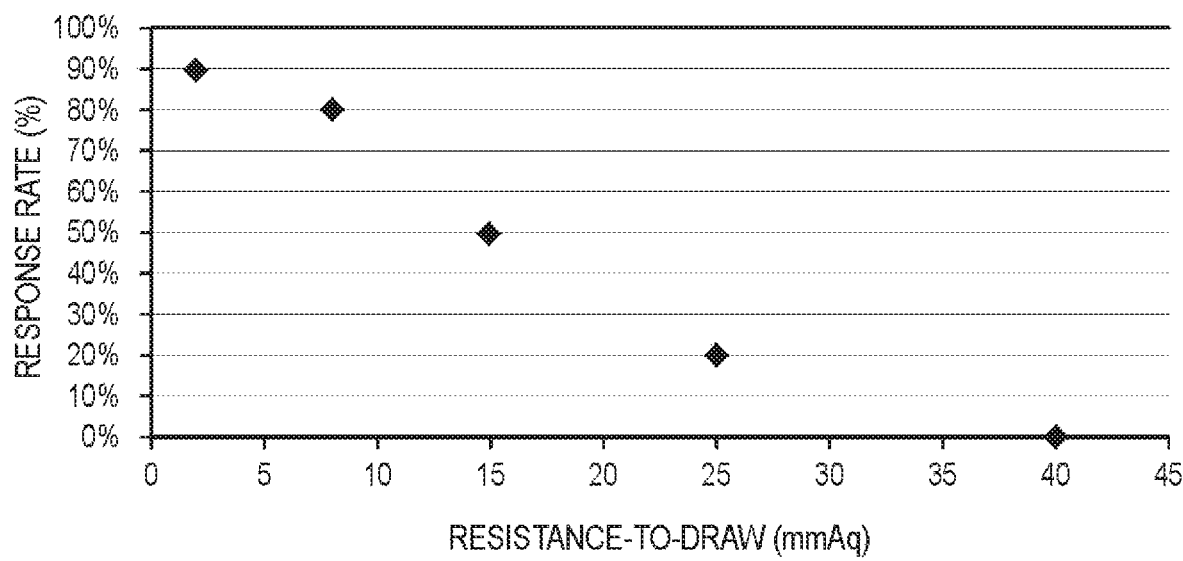

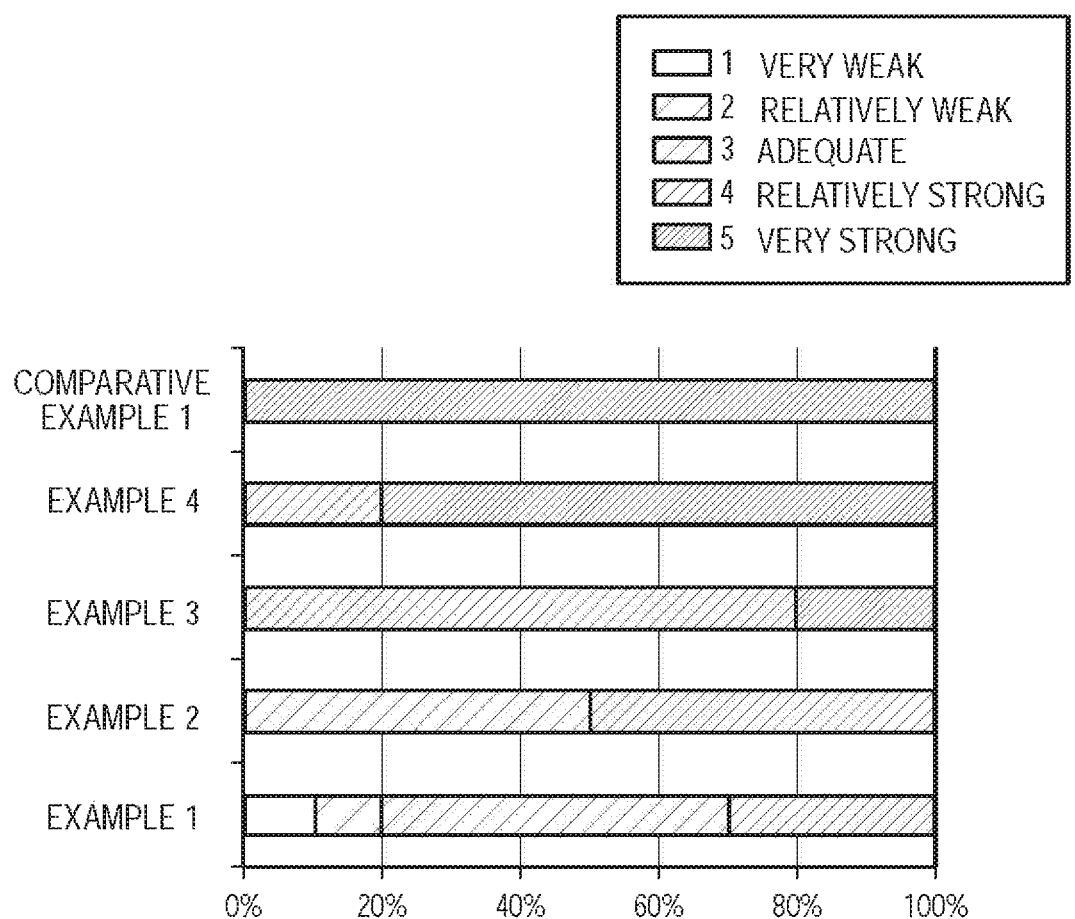

FLAVOR INHALER

CROSS REFERENCE TO RELATED APPLICATION

This application is a Continuation of PCT International Application No. PCT/JP2016/060251, filed on Mar. 29, 2016, which claims priority under 35 U.S.C. 119(a) to Patent Application No. PCT/JP2015/060493, filed in Japan on Apr. 2, 2015, all of which are hereby expressly incorporated by reference into the present application.

TECHNICAL FIELD

The present invention relates to a flavor inhaler having an atomizer configured to atomize an aerosol source.

BACKGROUND ART

Conventionally known is a flavor inhaler for inhaling flavor. For example, a flavor inhaler has an air flow path continuous from an inlet to an outlet, and an atomizer arranged in the air flow path and configured to atomize an aerosol source (for example, Patent Documents 1 and 2).

PRIOR ART DOCUMENT

Patent Document

Patent Document 1: WO2014/085719
Patent Document 2: WO2014/130772

SUMMARY OF THE INVENTION

A first feature is summarized as a flavor inhaler comprising: a housing having an air flow path continuous from an inlet to an outlet; and an atomizer configured to atomize an aerosol source without burning the aerosol source, wherein at least a part of the air flow path includes an aerosol flow path which is a flow path of an aerosol generated from the atomizer, and a resistance-to-draw of the entire air flow path is 25 mmAq or less.

A second feature according to the first feature is summarized as the flavor inhaler comprising: a switch for supplying a power source output to the atomizer during a period a user performs an inhaling action while not supplying the power source output to the atomizer during a period the user does not perform the inhaling action.

A third feature according to the second feature is summarized as the flavor inhaler comprising: a sensor configured to output a response value that changes in accordance with the inhaling action of the user, wherein the switch operates based on the response value output from the sensor.

A fourth feature according to the third feature is summarized as that the housing includes a first housing that houses the atomizer, and a second housing, removable from the first housing, that houses a power source configured to accumulate power supplied to the atomizer, and the sensor is housed in the second housing and provided on a side of the first housing relative to the power source.

A fifth feature according to the fourth feature is summarized as that the inlet is provided between the sensor and the atomizer.

A sixth feature according to any one of the third feature to the fifth feature is summarized as that the housing has a first hollow provided at a side same with the inlet and the outlet relative to the sensor, and a second hollow provided at an opposite side of the inlet and the outlet relative to the sensor, and the first hollow and the second hollow are partitioned not to communicate with each other within the housing.

A seventh feature according to any one of the third feature to the sixth feature is summarized as that an end threshold value to be compared with the response value to determine whether to operate the switch not to supply the power source output to the atomizer is larger than a start threshold value to be compared with the response value to determine whether to operate the switch to supply the power source output to the atomizer.

An eighth feature according to the second feature is summarized as the flavor inhaler comprising: an operation interface operated by a user, wherein the switch operates based on an operation on the operation interface.

A ninth feature according to any one of the first feature to the eighth feature is summarized as that the resistance-to-draw of the entire air flow path is 15 mmAq or less.

A tenth feature according to any one of the first feature to the ninth feature is summarized as that the resistance-to-draw of the entire air flow path is 2 mmAq or more and 8 mmAq or less.

An eleventh feature according to any one of the first feature to the tenth feature is summarized as that the air flow path includes a first air flow path passing through the atomizer and a second air flow path not passing through the atomizer, the inlet includes a first inlet configured to lead an air into the first air flow path and a second inlet configured to lead an air into the second air flow path, the outlet includes a first outlet configured to lead an air out from the first air flow path and a second outlet configured to lead an air out from the second air flow path, the second inlet is different from the first inlet, and the second inlet is communicable with the aerosol flow path at a side of the first outlet relative to the atomizer or communicates with the second outlet without communicating with the aerosol flow path.

A twelfth feature according to the eleventh feature is summarized as that an amount of air flowing in from the second inlet is 50% or more of an amount of air flowing out from the outlet.

A thirteenth feature according to the eleventh feature or the twelfth feature is summarized as that the housing includes an inhaler housing that houses at least the atomizer, and a cartridge housing that houses at least a flavor source provided on a side of the first outlet relative to the atomizer, the inhaler housing has the second inlet communicable with the aerosol flow path at a side of the first outlet relative to the atomizer, and the cartridge housing forms at least a part of the second air flow path.

A fourteenth feature according to the thirteenth feature is summarized as that the cartridge housing is configured to be inserted into the inhaler housing along a predetermined direction, the cartridge housing has a first recess portion formed on an outside surface adjacent to the inhaler housing, and the first recess portion is annularly continued in a cross section perpendicular to the predetermined direction at a position corresponding to the second inlet in the predetermined direction, and forms a part of the second air flow path.

A fifteenth feature according to the eleventh feature or the twelfth feature is summarized as that the housing includes an inhaler housing that houses at least the atomizer, and a cartridge housing that houses at least a flavor source provided on a side of the first outlet relative to the atomizer, and the inhaler housing has the second inlet communicating with the second outlet without communicating with the aerosol flow path.

A sixteenth feature according to the fourteenth feature is summarized as that the cartridge housing is configured to be inserted into the inhaler housing along a predetermined direction, the cartridge housing has a second recess portion formed on an outside surface adjacent to the inhaler housing, and the second recess portion is annularly continued in a cross section perpendicular to the predetermined direction at a position corresponding to the second inlet in the predetermined direction.

A seventeenth feature according to the eleventh feature or the twelfth feature is summarized as that the housing includes an inhaler housing that houses at least the atomizer, and a cartridge housing that houses at least a flavor source provided on a side of the first outlet relative to the atomizer, and the second inlet is provided at a cartridge protruding portion if the cartridge housing includes the cartridge protruding portion extending toward a side of the first outlet from the inhaler housing in the predetermined direction, or the second inlet is provided at an inhaler protruding portion if the inhaler housing includes the inhaler protruding portion extending toward the side of the first outlet from the cartridge housing in the predetermined direction.

An eighteenth feature according to any one of the eleventh feature to the seventeenth feature is summarized as the flavor inhaler comprising: a flavor source provided on a side of the first outlet relative to the atomizer, wherein the second inlet is provided on a side of the second outlet relative to the flavor source.

An nineteenth feature according to any one of the first feature to the eighteenth feature is summarized as the flavor inhaler comprising: a flavor source provided on a side of the outlet relative to the atomizer, wherein the aerosol flow path includes a first aerosol flow path configured to lead an aerosol toward a side of the outlet through the flavor source, and a second aerosol flow path different from the first aerosol flow path, and a reduction ratio of aerosol in the second aerosol flow path is smaller than a reduction ratio of aerosol in the first aerosol flow path.

A twentieth feature according to the nineteenth feature is summarized as that the second aerosol flow path is a flow path configured to lead an aerosol toward a side of the outlet without passing through the flavor source.

A twenty first feature according to any one of the first feature to the twentieth feature is summarized as the flavor inhaler comprising: a flavor source unit having a flavor source provided on a side of the outlet relative to the atomizer, wherein the housing has a shape extending along a predetermined direction, the flavor source unit is arranged in the housing to partition the aerosol flow path into a first space at the inlet side and a second space at the outlet, and an area of the flavor source unit being exposed to at least any one of the first space and the second space is larger than a cross section area defined by an inner circumference of the housing in a cross section perpendicular to the predetermined direction.

A twenty second feature according to the twenty first feature is summarized as that the flavor source unit partitions the first space and the second space along the predetermined direction, the flavor source unit has a first wall body being exposed to the first space and the second space, and a second wall body continuing to the first wall body, the first wall body is formed by a member having air permeability, and an area of an outer surface of the first wall body is larger than an area of an outer surface of the second wall body.

A twenty third feature according to any one of the first feature to the twenty second feature is summarized as that the flavor inhaler is configured to allow the resistance-to-draw of the entire air flow path to be changeable to 25 mmAq or less.

In the above features, a distance between the inlet and sensor may be 20 mm or less. The distance between the inlet and sensor may be preferably 15 mm or less and further preferably 10 mm or less.

BRIEF DESCRIPTION OF THE DRAWINGS

FIG. 16 is a diagram illustrating the atomizing unit 111 and the cartridge 130 according to the ninth modification.

FIG. 19 is a chart for describing an experiment result.
FIG. 20 is a chart for describing the experiment result.
FIG. 21 is a chart for describing the experiment result.
FIG. 22 is a chart for describing the experiment result.

DESCRIPTION OF THE EMBODIMENT

Figure 1:
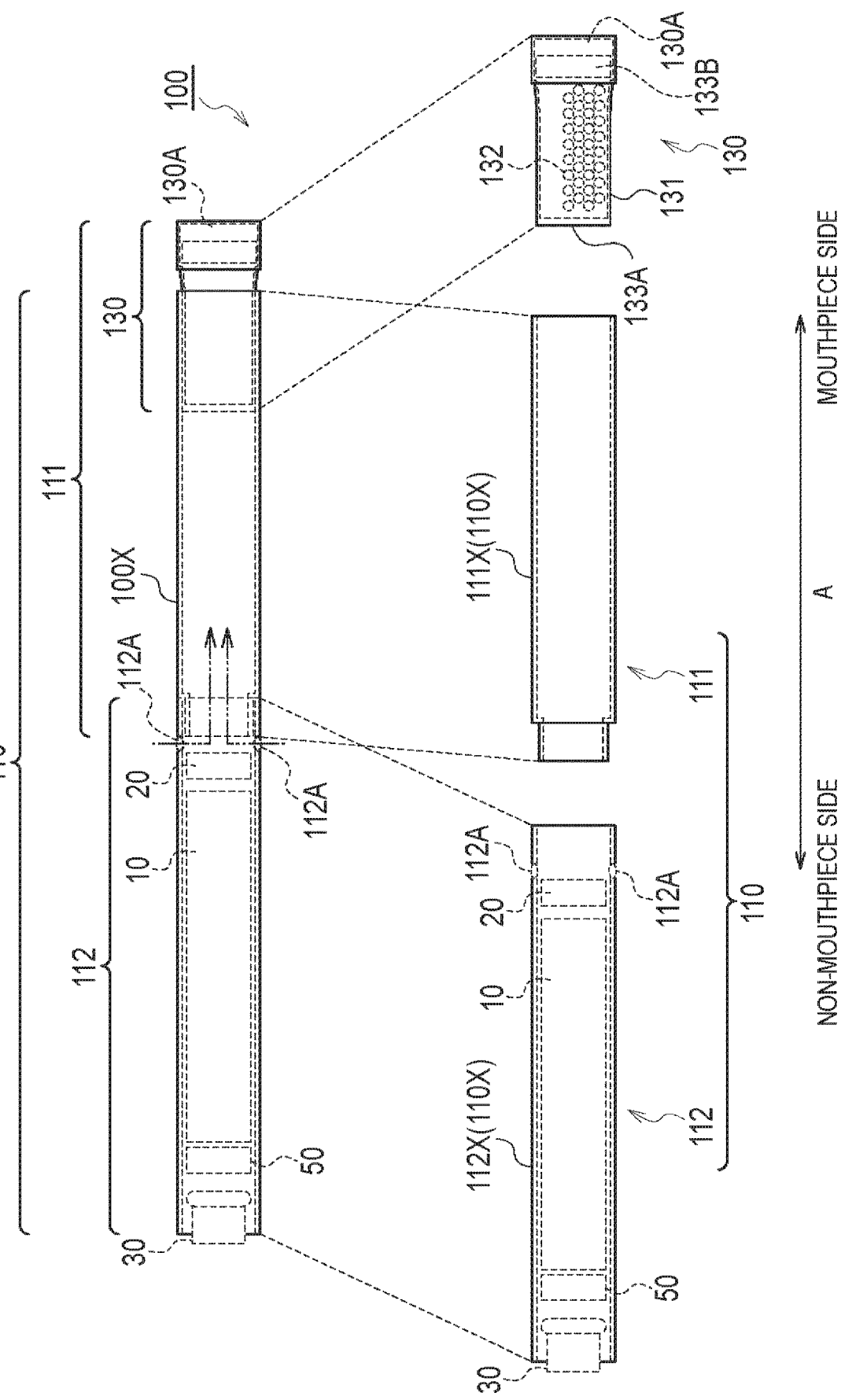
FIG. 1 is a diagram illustrating a non-burning type flavor inhaler 100 according to a first embodiment.

Hereinafter, embodiments of the present invention will be described. In the following description of the drawings, the same or similar reference numerals denote the same or similar parts. It should be noted that the drawings are schematic, and the ratios of dimensions and the like may be different from the actual ones.

Therefore, specific dimensions and the like may be determined by referring to the following description. Of course, the drawings may include the parts having different dimensions and ratios.

Overview of Embodiment

With the above-described BACKGROUND ART and as a result of extensive studies, the inventors found that during puff inhalation in which a user retains an aerosol in the mouth cavity, the loss of the aerosol source and the loss of the energy required for atomizing the aerosol source (hereinafter, these phenomena are collectively referred to as "aerosol loss") occur due to the leakage of the aerosol retained in the mouth cavity to outside the mouth cavity. As a result of extensive studies, the inventors further found that a factor for the user to perform puff inhalation is a resistance-to-draw of an air flow path.

A flavor inhaler according to the embodiment comprises: a housing having an air flow path continuous from an inlet to an outlet; and an atomizer configured to atomize an aerosol source without burning the aerosol source. At least a part of the air flow path includes an aerosol flow path which is a flow path of an aerosol generated from the atomizer. A resistance-to-draw of the entire air flow path is 25 mmAq or less.

In the embodiment, the resistance-to-draw of the entire air flow path is 25 mmAq or less, and thus, the puff inhalation in which the user retains the aerosol in the mouth cavity is not likely to be performed, but a direct inhaling action (hereinafter, referred to as direct inhalation) is likely to be performed. Therefore, the deterioration of the inhaling flavor can be suppressed by reducing the aerosol loss.

First Embodiment (Flavor Inhaler)

Figure 2:
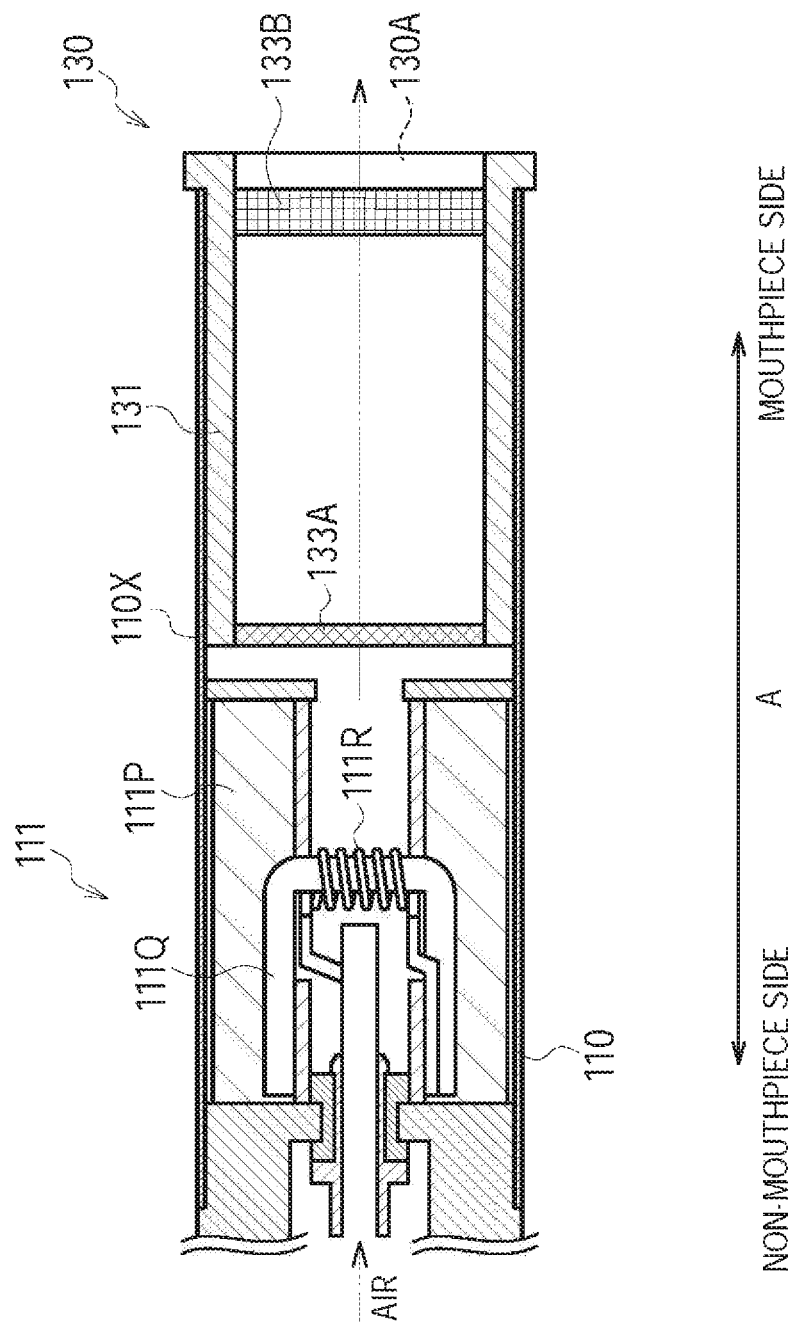
FIG. 2 is a diagram illustrating an atomizing unit 111 according to the first embodiment.

A flavor inhaler according to a first embodiment will be described, below. FIG. 1 is a diagram illustrating a non-burning type flavor inhaler 100 according to the first embodiment. The non-burning type flavor inhaler 100 is a device configured to be used to inhale an inhaling flavor component, and has a shape extending along a predetermined direction A that is a direction from a non-mouthpiece end toward a mouthpiece end. FIG. 2 is a diagram illustrating an atomizing unit 111 according to the first embodiment. It should be noted that hereinafter, the non-burning type flavor inhaler 100 will be simply called a flavor inhaler 100.

As illustrated in FIG. 1, the flavor inhaler 100 has an inhaler main unit 110 and a cartridge 130.

The inhaler main unit 110 is included in a main unit of the flavor inhaler 100, and has a shape allowing the cartridge 130 to be connected. Specifically, the inhaler main unit 110 has an inhaler housing 110X, and the cartridge 130 is connected to a mouthpiece side end of the inhaler housing 110X. The inhaler main unit 110 has an atomizing unit 111 and an electrical unit 112 configured to atomize an aerosol source without burning. The atomizing unit 111 and the electrical unit 112 are housed in the inhaler housing 110X.

In the first embodiment, the atomizing unit 111 has a first cylinder 111X (i.e., a first housing) forming a part of the inhaler housing 110X. As illustrated in FIG. 2, the atomizing unit 111 has a reservoir 111P, a wick 111Q, and an atomizer 111R. The reservoir 111P, the wick 111Q, and the atomizer 111R are housed in the first cylinder 111X. The first cylinder 111X has a tubular shape (for example, a cylindrical shape) extending along the predetermined direction A. The reservoir 111P retains an aerosol source. For example, the reservoir 111P is a porous body formed by a material such as a resin web. The wick 111Q is an example of an aerosol inhaling unit configured to absorb the aerosol source retained in the reservoir 111P. For example, the wick 111Q is formed by a glass fiber. The atomizer 111R atomizes the aerosol source absorbed by the wick 111Q. The atomizer 111R is, for example, formed by a heating resistor (for example, a heating wire) wound around the wick 111Q at a predetermined pitch.

The aerosol source is a liquid, such as glycerin or propylene glycol. The aerosol source is, for example, as described above, retained by a porous body formed by a material such as a resin web. The porous body may be formed by a non-tobacco material, or may be formed by a tobacco material. It is noted that the aerosol source may include a flavor source containing a nicotine component or the like. Alternatively, the aerosol source may not need to include the flavor source containing a nicotine component or the like. The aerosol source may include a flavor source containing a component other than the nicotine component. Alternatively, the aerosol source may not need to include the flavor source containing a component other than the nicotine component.

In the first embodiment, a heating type unit configured to atomize the aerosol source by heating is illustrated as the atomizing unit 111. However, as long as the atomizing unit 111 has a function of atomizing the aerosol source, the atomizing unit 111 may be an ultrasonic wave type unit configured to atomize the aerosol source by an ultrasonic wave.

The electrical unit 112 has a second cylinder 112X (i.e., a second housing) forming a part of the inhaler housing 110X. In the first embodiment, the electrical unit 112 has an inlet 112A. As illustrated in FIG. 2, the air flowing in from the inlet 112A is led into the atomizing unit 111 (atomizer 111R). In particular, the electrical unit 112 has a power source 10, a sensor 20, a push button 30, and a control circuit 50. The power source 10, the sensor 20, the push button 30, and the control circuit 50 are housed in the second cylinder 112X. The second cylinder 112X has a tubular shape (for example, a cylindrical shape) extending along the predetermined direction A.

The power source 10 is, for example, a lithium ion battery. The power source 10 accumulates the power necessary for the operation of the flavor inhaler 100. For example, the power source 10 accumulates the power supplied to the sensor 20 and the control circuit 50. Moreover, the power source 10 accumulates the power supplied to the atomizing unit 111 (atomizer 111R).

The sensor 20 is a sensor for detecting an inhaling action of a user (an inhalation sensor, a flow rate sensor, a pressure sensor, etc.). The sensor 20 outputs a response value that changes in accordance with air inhaled from the non-mouthpiece end toward the mouthpiece end (i.e., the inhaling action of the user).

The push button 30 is configured to be pushed from the outer side of the flavor inhaler 100 toward the inner side thereof. In the embodiment, the push button 30 is provided at the non-mouthpiece end of the flavor inhaler 100, and is configured to be pushed in a direction from the non-mouthpiece end toward the mouthpiece end (i.e., the predetermined direction A). For example, if the push button 30 is pushed continuously over a predetermined number of times, the power source of the flavor inhaler 100 is turned on. It is noted that the power source of the flavor inhaler 100 is disconnected if a predetermined time elapses from an inhaling action being performed.

The control circuit 50 controls the operation of the flavor inhaler 100. Specifically, the control circuit 50 controls the power source output to the atomizing unit 111 (atomizer 111R).

The cartridge 130 is capable of connecting to the inhaler main unit 110 forming the flavor inhaler 100. The cartridge 130 is provided on the outlet (mouthpiece) side relative to the atomizing unit 111 on an air flow path continuous from an inlet (the above-described inlet 112A in the first embodiment) to an outlet (an outlet 130A described later in the first embodiment). In other words, the cartridge 130 may not necessarily be provided, in terms of a physical space, on the outlet (mouthpiece) side relative to the atomizing unit 111, but it may be sufficient that the cartridge 130 is provided on the outlet (mouthpiece) side relative to the atomizing unit 111 on the air flow path. That is, in the first embodiment, the "outlet (mouthpiece) side" may be considered to be synonymous with a "downstream" of an air flow during the inhaling action, and the "non-mouthpiece side" may be considered to be synonymous with an "upstream" of the air flow during the inhaling action.

Specifically, the cartridge 130 has a cartridge housing 131, a flavor source 132, a mesh 133A, and a filter 133B. The cartridge 130 further has an outlet 130A provided at the mouthpiece.

The cartridge housing 131 has a tubular shape (for example, a cylindrical shape) extending along the predetermined direction A. The cartridge housing 131 houses the flavor source 132. Here, the cartridge housing 131 is configured to be inserted along the predetermined direction A into the inhaler housing 110X.

The flavor source 132 is provided on the outlet 130A (mouthpiece) side relative to the atomizing unit 111 on the air flow path continuous from the inlet 112A to the outlet 130A. The flavor source 132 imparts an inhaling flavor component to the aerosol generated from the aerosol source. In other words, the inhaling flavor component imparted to the aerosol by the flavor source 132 is carried to the outlet 130A (mouthpiece).

In the first embodiment, the flavor source 132 is formed by raw material pieces that impart the inhaling flavor component to the aerosol generated from the atomizing unit 111. The size of the raw material pieces is preferably from 0.2 mm to 1.2 mm. Furthermore, the size of the raw material pieces is preferably from 0.2 mm to 0.7 mm. The smaller the size of the raw material pieces included in the flavor source 132, the more the specific surface area, therefore an inhaling flavor component is more easily released from the raw material pieces included in the flavor source 132. Therefore, the amount of raw material pieces can be controlled when imparting a desired amount of the inhaling flavor component to the aerosol. It is possible to use shredded tobacco or a formed body in which a tobacco raw material is granularly formed as the raw material pieces included in the flavor source 132. However, the flavor source 132 may be a formed body in which the tobacco raw material is formed into a sheet. Moreover, the raw material pieces included in the flavor source 132 may be formed by a plant other than tobacco (for example, mint and herbs). Flavorings such as menthol may be added to the flavor source 132.

Here, for example, the raw material pieces included in the flavor source 132 are obtained, for example, by sieving that complies with JIS Z 8815 using a stainless steel sieve that complies with JIS Z 8801. For example, raw material pieces passing through a stainless steel sieve having sieve openings of 0.71 mm are obtained by sieving the raw material pieces over 20 minutes by a drying and mechanical shaking method using the stainless steel sieve having the sieve openings of 0.71 mm. Subsequently, raw material pieces passing through a stainless steel sieve having sieve openings of 0.212 mm are removed by sieving the raw material pieces over 20 minutes by the drying and mechanical shaking method using the stainless steel sieve having the sieve openings of 0.212 mm. That is, the raw material pieces included in the flavor source 132 are raw material pieces passing through a stainless steel sieve (sieve openings=0.71 mm) that regulates an upper limit and do not pass through a stainless steel sieve (sieve openings=0.212 mm) that regulates a lower limit. Accordingly, in the embodiment, the lower limit of the size of the raw material pieces included in the flavor source 132 is defined by the sieve openings of a stainless steel sieve that regulates the lower limit. It is noted that the upper limit of the size of the raw material pieces included in the flavor source 132 is defined by the sieve openings of a stainless steel sieve that regulates the upper limit.

In the first embodiment, the flavor source 132 is a tobacco source having an alkaline pH. The pH of the tobacco source is preferably more than 7, and more preferably 8 or above. By increasing the pH beyond 7, the inhaling flavor component generated from the tobacco source can be taken effectively by aerosol. As a result, the amount of the tobacco source can be controlled when imparting a desired amount of the inhaling flavor component to the aerosol. On the other hand, the pH of the tobacco source is preferably 14 or less, and more preferably 10 or less. By keeping the pH at 14 or less, the damage (such as corrosion) to the flavor inhaler 100 (for example, the cartridge 130 or the inhaler main unit 110) can be suppressed more effectively.

It should be noted that the inhaling flavor component generated from the flavor source 132 is transported by the aerosol, and that there is no need of heating the flavor source 132 itself.

The mesh 133A is provided to close the opening of the cartridge housing 131 at the non-mouthpiece side with respect to the flavor source 132, and the filter 133B is provided to cover the opening of the cartridge housing 131 at the mouthpiece side with respect to the flavor source 132. The mesh 133A is so rough that the raw material pieces included in the flavor source 132 do not pass through. The roughness of the mesh 133A includes openings from 0.077 mm to 0.198 mm, for example. The filter 133B is formed by a material having air permeability. The filter 133B is preferably an acetate filter, for example. The filter 133B is so rough that the raw material pieces included in the flavor source 132 do not pass through.

In the first embodiment, the inhaler housing 110X of the inhaler main unit 110 and the cartridge housing 131 form a housing having the air flow path continuous from the inlet 112A to the outlet 130A. At least a part of the air flow path (i.e., a flow path at the downstream side of the atomizer 111R illustrated in FIG. 2) includes an aerosol flow path that is a flow path of an aerosol generated from the atomizing unit 111.

In such a case, the resistance-to-draw of the entire air flow path is 25 mmAq or less. Preferably, the resistance-to-draw of the entire air flow path is 15 mmAq or less. More preferably, the resistance-to-draw of the entire air flow path is 2 mmAq or more and 8 mmAq or less. The smaller the resistance-to-draw is, the more likely the puff inhalation in which the user retains the aerosol in the mouth cavity is not performed, and the more likely the direct inhaling action (direct inhalation) is performed. It should be noted that 1 mmAq corresponds to 9.80665 Pa.

Here, the resistance-to-draw is measured by using a method conforming to ISO 6565-1997 Draw resistance of cigarettes and pressure drop of filter rods. Specifically, the resistance-to-draw is defined as pressure loss at the time of performing inhalation at 1050 mL/min by a vacuum pump, when the flavor inhaler 100, a differential pressure gauge, a mass flow controller, and the vacuum pump are connected in this order from the upstream side of the air flow path.

It is noted that the resistance-to-draw of the entire air flow path is preferably 0.5 mmAq or more. Furthermore, the resistance-to-draw of the entire air flow path is preferably a value equal to or higher than a value allowing the above-described sensor 20 to detect the inhaling action.

(Block Configuration)

Figure 3:
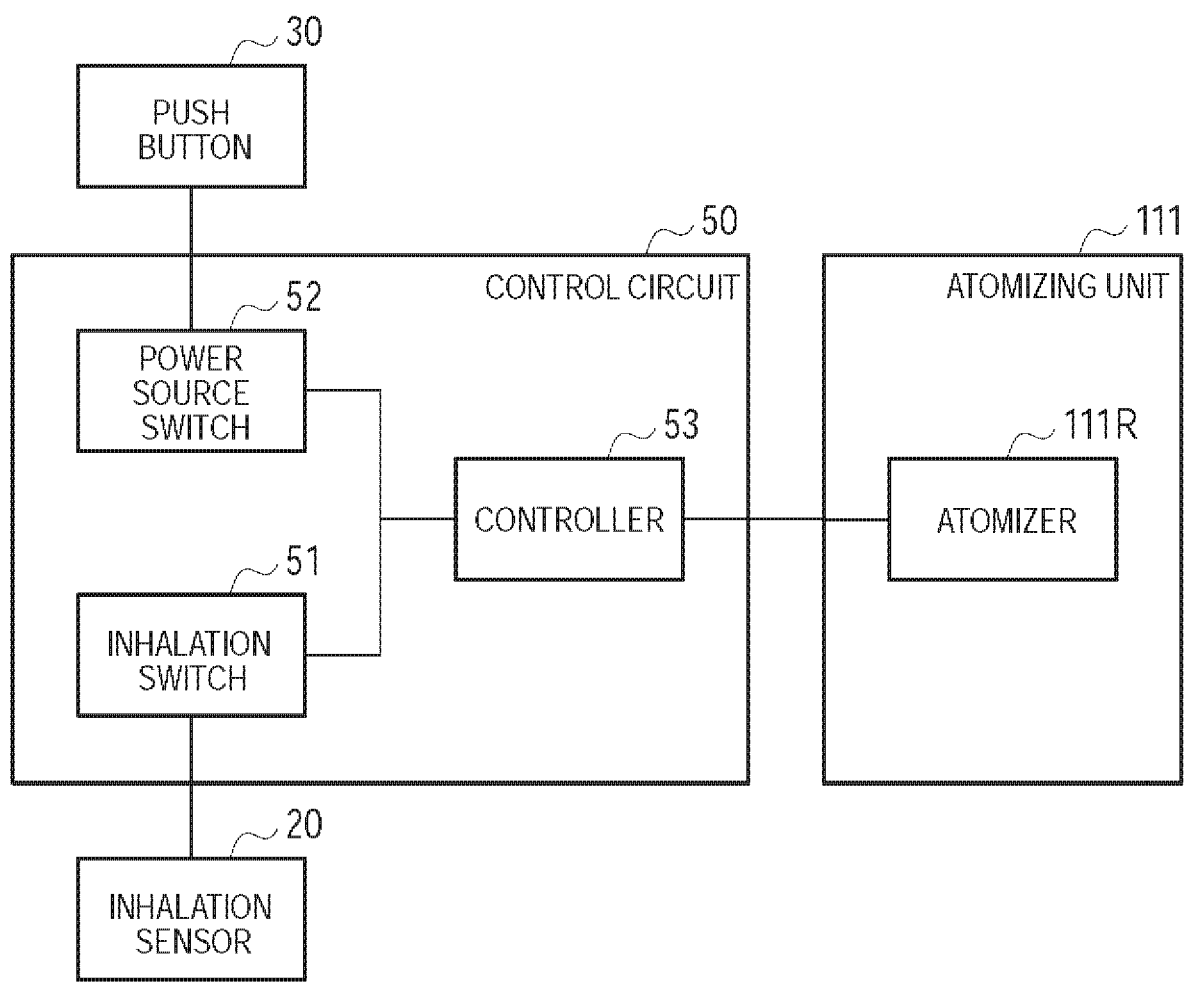
FIG. 3 is a diagram illustrating a block configuration of the non-burning type flavor inhaler 100 according to the first embodiment.

A block configuration of the flavor inhaler according to the first embodiment will be described, below. FIG. 3 is a diagram illustrating the block configuration of the flavor inhaler 100 according to the first embodiment.

As illustrated in FIG. 3, the control circuit 50 has an inhalation switch 51, a power source switch 52, and a controller 53.

The inhalation switch 51 is a switch configured to be switched to an ON state during a period the user performs the inhaling action, and switched to an OFF state during a period the user does not perform the inhaling action. Specifically, the inhalation switch 51 is connected to the sensor 20 for detecting the inhaling action of the user, and operates based on a response value output from the sensor 20. That is, the inhalation switch 51 is switched to the ON state if the response value indicates that the inhaling action is being performed. Meanwhile, the inhalation switch 51 is switched to the OFF state if the response value indicates that the inhaling action is not being performed.

The power source switch 52 is switched to an ON state if the power source of the non-burning type flavor inhaler 100 is turned on, and is switched to an OFF state if the power source of the non-burning type flavor inhaler 100 is turned off. Specifically, the power source switch 52 is connected to the push button 30, and is switched to the ON state if the push button 30 is pushed continuously over a predetermined number of times. Meanwhile, the power source switch 52 has a timer, and is switched to the OFF state if a predetermined time elapses from the inhaling action being performed.

The controller 53 controls the non-burning type flavor inhaler 100 in a state where the power source of the non-burning type flavor inhaler 100 is turned on. Specifically, the controller 53 controls the power source output to the atomizer 111R. The controller 53 supplies the power source output to the atomizer 111R during a period the user performs the inhaling action, i.e., during a period the inhalation switch 51 is in the ON state. Meanwhile, the controller 53 does not supply the power source output to the atomizer 111R during a period the user does not perform the inhaling action, i.e., during a period the inhalation switch 51 is in the OFF state. That is, the inhalation switch 51 is a switch for supplying the power source output to the atomizer 111R during the period the user performs the inhaling action while not supplying the power source output to the atomizer 111R during the period the user does not perform the inhaling action.

Here, upon the voltage being applied continuously to the atomizer 111R, the magnitude of the power source output is defined by a value of the voltage applied to the atomizer 111R. Meanwhile, upon the voltage being applied intermittently to the atomizer 111R (pulse control), the magnitude of the power source output is defined by at least any one of parameters of the value of the voltage applied to the atomizer 111R, the pulse width, and the pulse interval.

Here, an end threshold value is larger than a start threshold value. The end threshold value is a threshold value to be compared with the response value output from the sensor 20 to determine whether to operate the inhalation switch 51 not to supply the power source output to the atomizer 111R, i.e., a threshold value to be compared with the response value to determine whether to turn OFF the inhalation switch 51. Meanwhile, the start threshold value is a threshold value to be compared with the response value output from the sensor 20 to determine whether to operate the inhalation switch 51 to supply the power source output to the atomizer 111R, i.e., a threshold value to be compared with the response value to determine whether to turn ON the inhalation switch 51. According to the above-described features, the end threshold value is larger than the start threshold value, and thus, the actual inhaling action is continued even after the supply of the power source output to the atomizer 111R is stopped. Therefore, the stagnation and condensation of the aerosol in the aerosol flow path are suppressed, and thus, the aerosol loss is suppressed. Meanwhile, the start threshold value is smaller than the end threshold value, and thus, the supply of the power source output to the atomizer 111R is quickly started after the actual inhaling action is started.

(Operation and Effect)

In the first embodiment, the resistance-to-draw of the entire air flow path is 25 mmAq or less, and thus, the puff inhalation in which the user retains the aerosol in the mouth cavity is not likely to be performed, but the direct inhaling action (direct inhalation) is likely to be performed. Therefore, the deterioration of the inhaling flavor can be suppressed by reducing the aerosol loss.

[First Modification]

A first modification of the first embodiment will be described, below. Differences from the first embodiment will be mainly described, below.

In the first modification, the air flow path includes a first air flow path passing through the atomizer 111R and a second air flow path not passing through the atomizer 111R. The inlet includes the inlet 112A (first inlet) configured to lead the air into the first air flow path and an inlet 80 (second inlet) configured to lead the air into the second air flow path. The outlet includes the outlet 130A (first outlet) configured to lead the air out from the first air flow path and an outlet 130A (second outlet) configured to lead the air out from the second air flow path. The inlet 80 (second inlet) is different from the inlet 112A (first inlet). It is noted that the aerosol flow path forms a part of the first air flow path.

Figure 4:
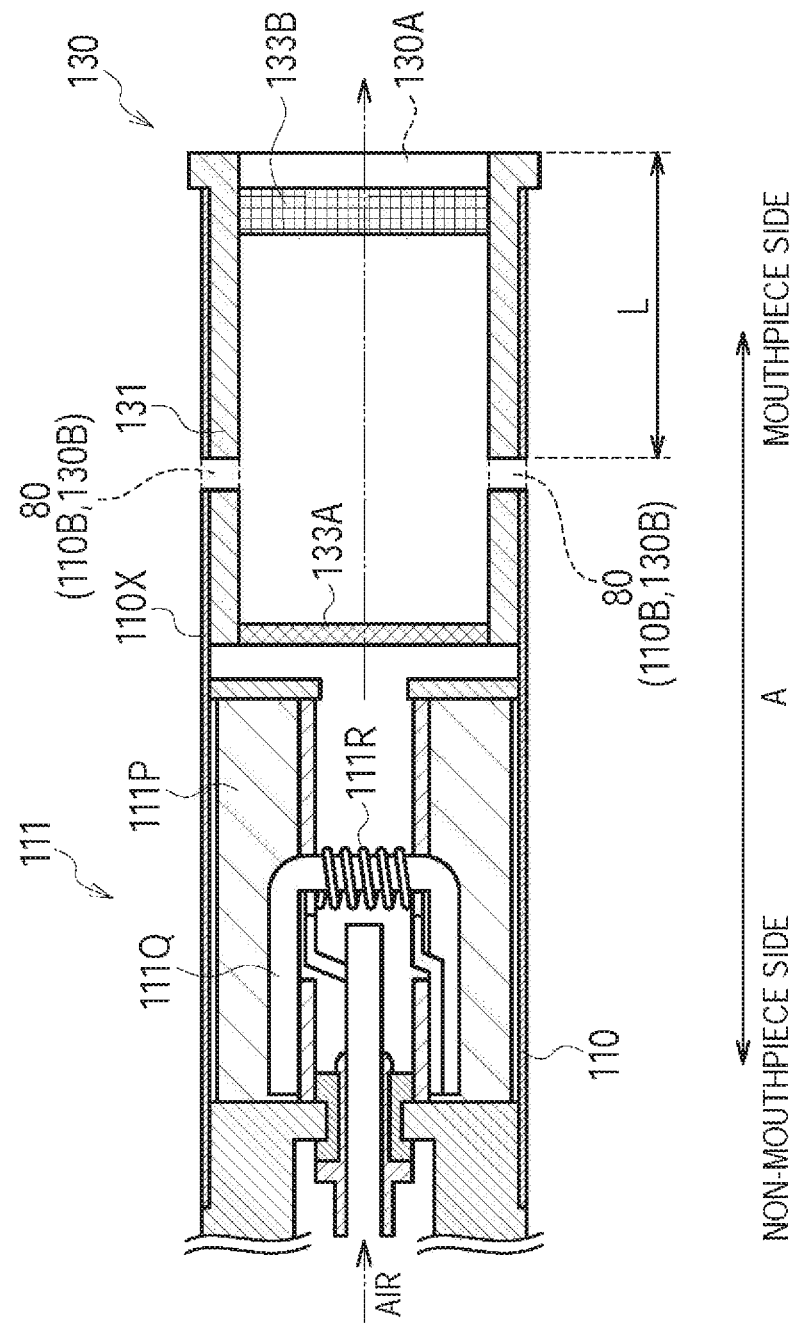
FIG. 4 is a diagram illustrating the atomizing unit 111 and a cartridge 130 according to a first modification.

Specifically, the cartridge housing 131 is configured to be inserted along the predetermined direction A into the inhaler housing 110X. As illustrated in FIG. 4, the inhaler housing 110X has an inhaler through hole 110B penetrating the inhaler housing 110X in a direction crossing the predetermined direction A, and the cartridge housing 131 has a cartridge through hole 130B penetrating the cartridge housing 131 in the direction crossing the predetermined direction A. The inhaler through hole 110B and the cartridge through hole 130B form the inlet 80 (second inlet), and communicate with an internal space of the cartridge housing 131.

In this regard, the inhaler through hole 110B is communicable with the aerosol flow path toward the outlet 130A side from the atomizer 111R. Here, "communicable" means that the inhaler through hole 110B communicates with the air flow path by correctly inserting the cartridge housing 131 into the inhaler housing 110X. Therefore, it should be noted that the inhaler through hole 110B may possibly not communicate with the air flow path depending on a state how the cartridge housing 131 is inserted into the inhaler housing 110X. However, it should also be noted that "communicable" includes a state in which the inhaler through hole 110B always communicates with the air flow path, as described in second and third modifications later.

In the first modification, the inlet 80 is provided separately from the inlet 112A. The inlet 80 is preferably provided on the mouthpiece side relative to the atomizer 111R, in terms of a spatial arrangement unrelated to the upstream/downstream of the air flow path. The outlet 130A forms both of the first outlet configured to lead the air out from the first air flow path and the second outlet configured to lead the air out from the second air flow path.

It is noted that in the first modification, the second air flow path is formed by the inlet 80 (the inhaler through hole 110B and the cartridge through hole 130B), a part of the aerosol flow path (the internal space of the cartridge housing 131), and the outlet 130A.

It is noted that the cartridge through hole 130B is preferably formed by one or more holes having a size such that raw material pieces included in the flavor source 132 do not pass through. Alternatively, the cartridge through hole 130B preferably has a mesh having the roughness such that the raw material pieces included in the flavor source 132 do not pass through. The size such that the raw material pieces do not pass through is, for example, an opening of 0.077 mm or more and 0.198 mm or less, and the roughness such that the raw material pieces do not pass through is, for example, a mesh having an opening of 0.077 mm or more and 0.198 mm or less.

Here, the amount of air flowing in from the inlet 80 (the inhaler through hole 110B and the cartridge through hole 130B) is preferably equal to or more than 50% of the amount of air flowing out from the outlet 130A. In other words, the amount of air flowing in from the inhaler through hole 110B is preferably equal to or more than the amount of air flowing in from the inlet 112A. More preferably, the amount of air flowing in from the inlet 80 is equal to or more than 60% of the amount of air flowing out from the outlet 130A. As a result, even if the air flowing in from the inlet 112A passes through the atomizer 111R, the resistance-to-draw of the entire air flow path can be easily suppressed to 25 mmAq or less.

In such a case, a distance L between a mouthpiece end of a housing (here, the mouthpiece end of the cartridge housing 131) having an air flow path in the predetermined direction A and the inlet 80 (second inlet) is preferably 1.5 mm or more. Furthermore, the distance L is preferably 3.0 mm or more, and more preferably 5.0 mm or more. Most preferably, the distance L is 8.0 mm or more. As a result, upon the user holding the flavor inhaler 100 in the mouth, situations are suppressed where the inhaler through hole 110B is blocked by the user's lips or the inhaler through hole 110B reaches inside the user's mouth cavity.

Meanwhile, the distance L is preferably shorter than a distance between the mouthpiece end of the housing (here, the mouthpiece end of the cartridge housing 131) having the air flow path in the predetermined direction A and the inlet 112A (first inlet). The distance L may be shorter than the entire length of the cartridge 130 in a predetermined direction. The entire length of the cartridge 130 is preferably 5 mm or more and 30 mm or less, and more preferably 10 mm or more and 25 mm or less. By assuming to be shorter than the entire length of the cartridge 130, the distance L is preferably less than 25 mm, for example. Furthermore, the distance L is preferably less than 20 mm, and more preferably less than 15 mm. Most preferably, the distance L is less than 10 mm. As a result, the resistance-to-draw of the entire air flow path can be easily controlled to 25 mmAq or less.

Moreover, the inhaler through hole 110B provided on the housing may be one, or may be two or more. That is, the number of inhaler through holes 110B is not particularly limited.

(Operation and Effect)

In the first modification, the non-burning type flavor inhaler 100 has the second air flow path not passing through the atomizer 111R, in addition to the first air flow path passing through the atomizer 111R. Therefore, even if the air flowing in from the inlet 112A passes through the atomizer 111R, the resistance-to-draw of the entire air flow path can be easily suppressed to 25 mmAq or less.

In the first modification, the amount of air flowing in from the inlet 80 is equal to or more than 50% of the amount of air flowing out from the outlet 130A. Therefore, even if the air flowing in from the inlet 112A passes through the atomizer 111R, the resistance-to-draw of the entire air flow path can be easily suppressed to 25 mmAq or less.

[Second Modification]

A second modification of the first embodiment will be described, below. Differences from the first modification will be mainly described, below.

Figure 5:
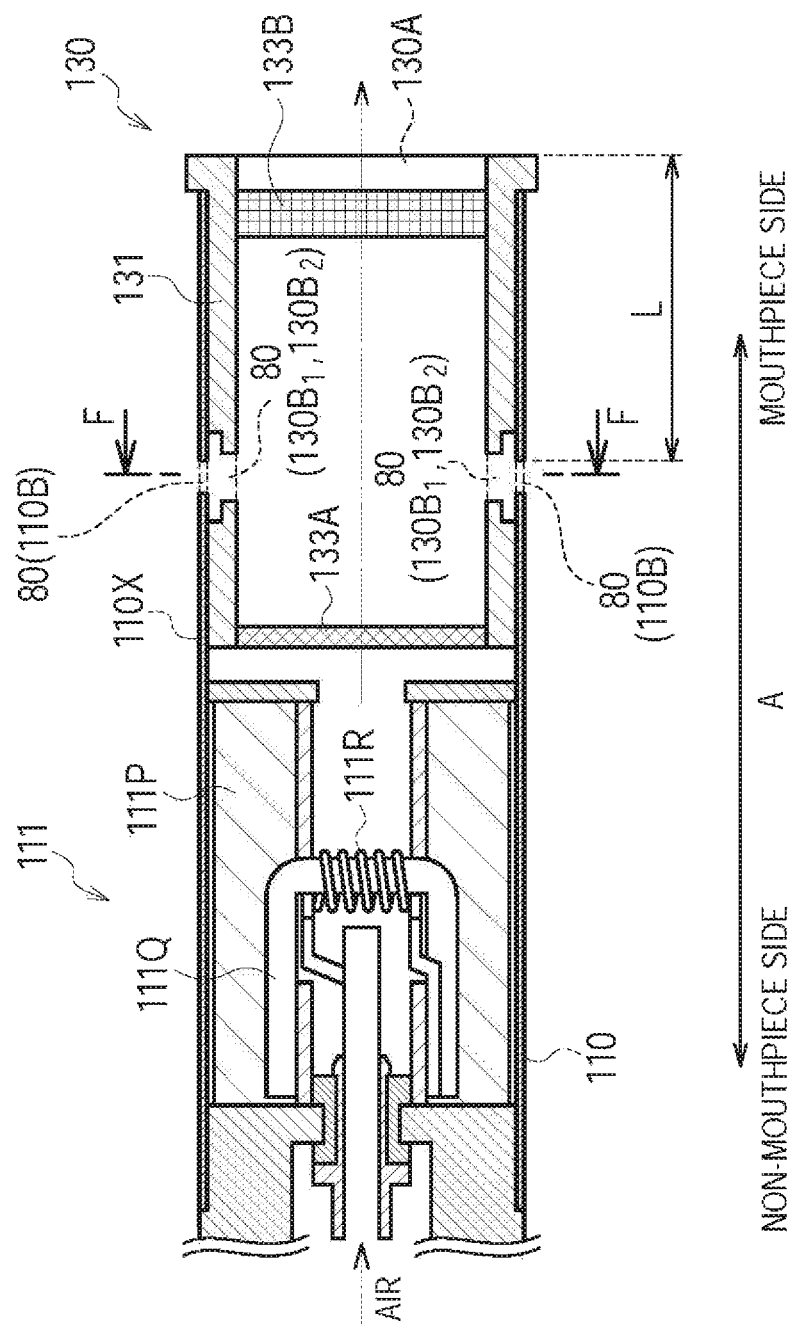
FIG. 5 is a diagram illustrating the atomizing unit 111 and the cartridge 130 according to a second modification.
Figure 6:
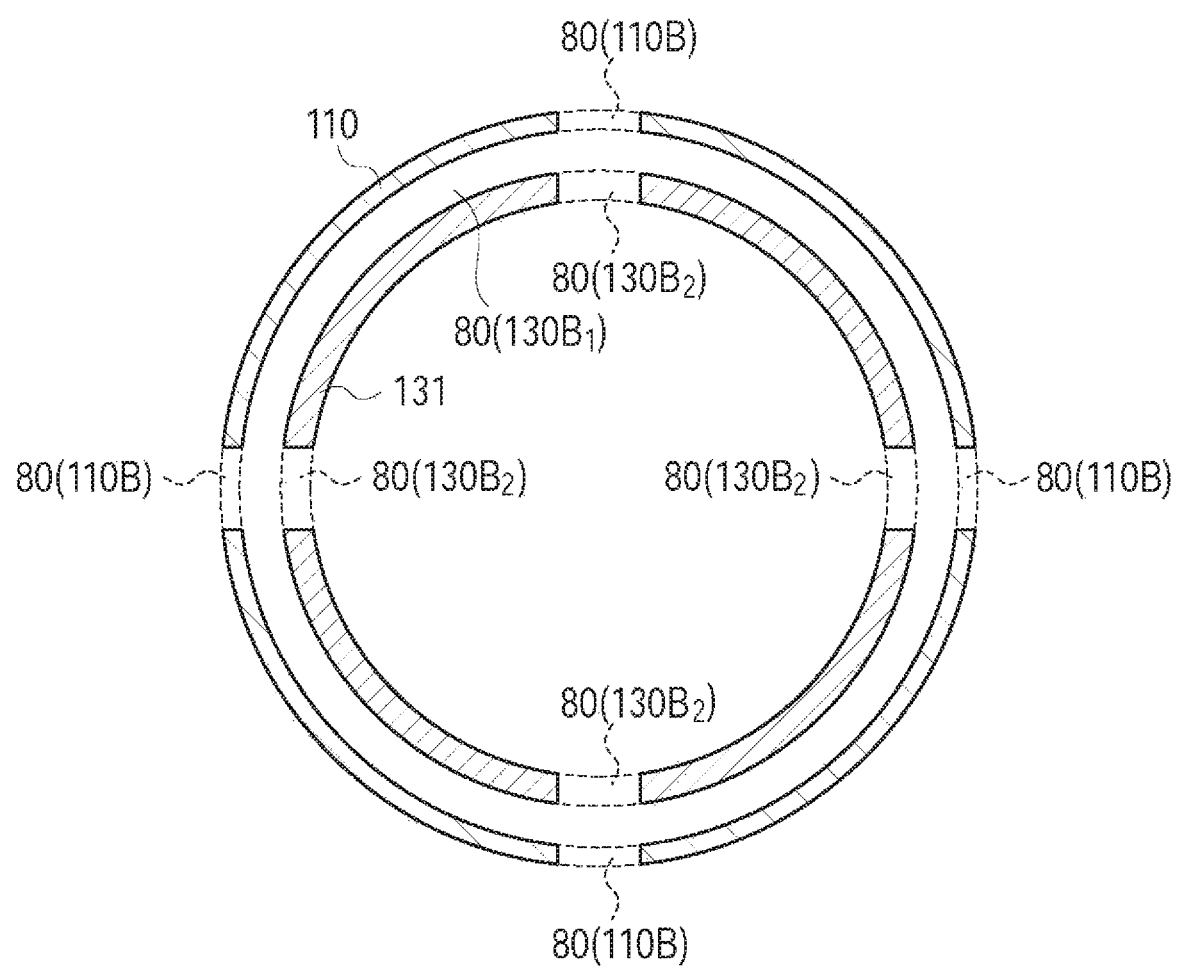
FIG. 6 is a diagram illustrating the atomizing unit 111 and the cartridge 130 according to the second modification.

In the first modification, the inlet 80 is formed by the inhaler through hole 110B and the cartridge through hole 130B. However, in the second modification, the inlet 80 is formed by the inhaler through hole 110B, a cartridge recess portion 130B1, and a cartridge through hole 130B2, as illustrated in FIG. 5 and FIG. 6. The cartridge recess portion $130B_1$ is provided to surround the entire circumference of the cartridge housing 131 in a cross section perpendicular to the predetermined direction A. The cartridge through hole 130B2 is provided at the cartridge recess portion 130B1. It is noted that FIG. 6 illustrates an F-F cross section (i.e., a perpendicular cross section with respect to the predetermined direction A) illustrated in FIG. 5.

Specifically, the cartridge housing 131 is configured to be inserted along the predetermined direction A into the inhaler housing 110X. As illustrated in FIG. 5 and FIG. 6, the cartridge housing 131 has the cartridge recess portion $130B_1$ (first recess portion) formed on an outside surface adjacent to the inhaler housing 110X, and the cartridge through hole $130B_2$ penetrating the cartridge recess portion $130B_1$ in a direction crossing the predetermined direction A. The cartridge recess portion $130B_1$ (first recess portion) is annularly continued in the cross section perpendicular to the predetermined direction A at a position where the inhaler through hole 110B is provided in the predetermined direction A.

Here, "annularly continued" may be a state not continued, in the cross section perpendicular to the predetermined direction A, over the entire length in the circumferential direction)(360°) around the predetermined direction A. For example, the cartridge recess portion $130B_1$ may be partitioned by discontinuous portions in the circumferential direction. It is noted that, in the circumferential direction, it may be sufficient that each width of the cartridge recess portion $13013_1$ partitioned by the discontinuous portions is wider than the interval between the inhaler through holes 110B adjacent to each other (the closest interval). Alternatively, in the circumferential direction, it may be sufficient that the width of the inhaler through hole 110B is wider than the width of the discontinuous portions.

It is noted that in the second modification, the second air flow path is formed by the inlet 80 (the inhaler through hole 110B, the cartridge recess portion 130B$_1$, and the cartridge through hole 130B2), a part of the aerosol flow path (the internal space of the cartridge housing 131), and the outlet 130A.

In the second modification, the cartridge recess portion 130B$_1$ is configured by reducing the thickness of the cartridge housing 131. However, the second modification is not limited thereto. It may be sufficient that the cartridge recess portion 130B$_1$ is configured such that the space is formed between an inside surface of the inhaler housing 110X and an outside surface of the cartridge housing 131. For example, if the cartridge housing 131 has a fixed thickness and has a recess portion internally recessed in the cross section perpendicular to the predetermined direction A, such recess portion may be employed as the cartridge recess portion 130B$_1$.

(Operation and Effect)

In the second modification, the inlet 80 includes the cartridge recess portion 130B$_1$ annularly continued in the cross section perpendicular to the predetermined direction A. Therefore, in addition to a similar effect to that of the first modification, even if the cartridge housing 131 is inserted into the inhaler housing 110X without paying attention to a relative position of the cartridge housing 131 and the inhaler housing 110X in a rotation direction of the cartridge housing 131, the inhaler through hole 110B communicates with the cartridge recess portion 130B1, and thus, the second air flow path can be always formed.

[Third Modification]

A third modification of the first embodiment will be described, below. Differences from the first modification will be mainly described, below.

In the first modification, the second air flow path includes a part of the aerosol flow path (the internal space of the cartridge housing 131). In other words, in the first modification, the inhaler through hole 110B and the cartridge through hole 130B form the inlet 80 (second inlet) and communicate with the internal space of the cartridge housing 131. However, in the third modification, the second air flow path does not include a part of the aerosol flow path (the internal space of the cartridge housing 131). In other words, in the third modification, the inhaler through hole 110B forms the inlet 80 (second inlet), and communicates with an outlet 130A$_1$ (second outlet) without communicating In the third modification, the inlet 80 is provided separately from the inlet 112A. The inlet 80 is preferably provided on the mouthpiece side relative to the atomizer 111R, in terms of a spatial arrangement unrelated to the upstream/downstream of the air flow path. The outlet 130A forms the first outlet configured to lead the air out from the first air flow path, and the outlet 130A$_1$ is provided separately from the outlet 130A and forms the second outlet configured to lead the air out from the second air flow path. The outlet 130A$_1$ and the outlet 130A are provided at the mouthpiece.

Figure 7:
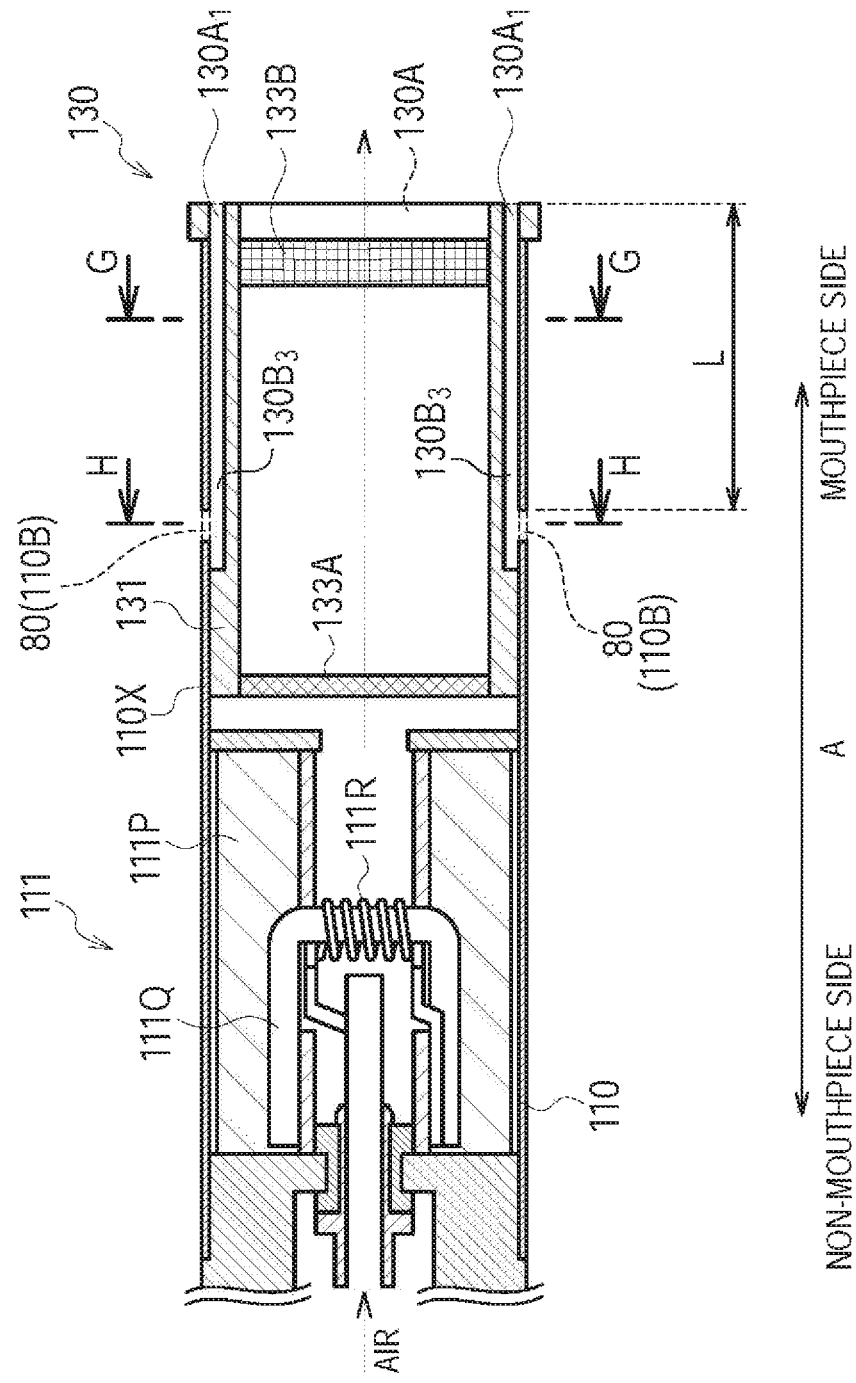
FIG. 7 is a diagram illustrating the atomizing unit 111 and the cartridge 130 according to a third modification.

Specifically, the cartridge housing 131 is configured to be inserted along the predetermined direction A into the inhaler housing 110X. As illustrated in FIG. 7, the cartridge housing 131 forms at least a part of the second air flow path not having a flow path common to the aerosol flow path. Specifically, the cartridge housing 131 has a cartridge recess portion 130B$_3$ (second recess portion) formed on the outside surface adjacent to the inhaler housing 110X. The cartridge recess portion 130B$_3$ is preferably continuous, along the predetermined direction A, from the inhaler through hole 110B (second inlet) to the outlet 130A$_1$ (second outlet). The cartridge recess portion 130B$_3$ forms a part of the second air flow path.

Figure 8:
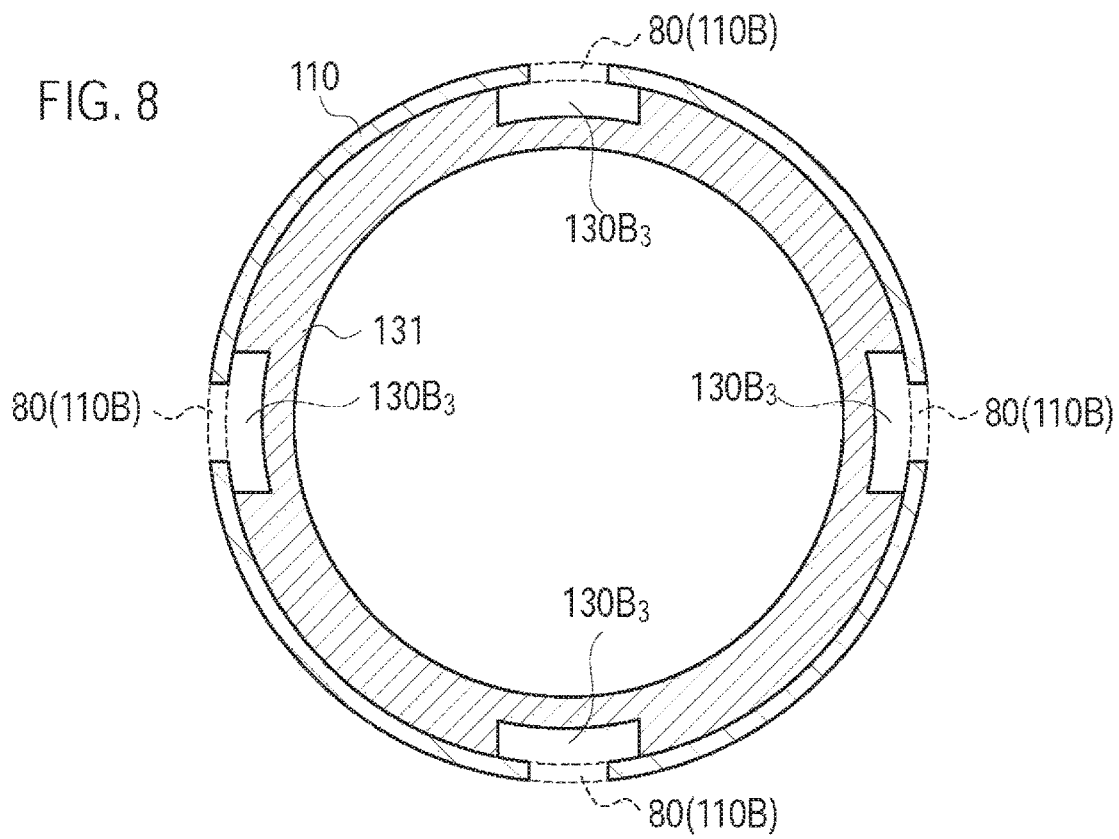
FIG. 8 is a diagram illustrating the atomizing unit 111 and the cartridge 130 according to the third modification.

In such a case, as illustrated in FIG. 8, the cartridge recess portion 130B$_3$ may be provided at a position corresponding to the inhaler through hole 110B. For example, in FIG. 8, four inhaler through holes 110B are illustrated, and four cartridge recess locations 130B$_3$ are provided at positions corresponding to these inhaler through holes 110B. In the circumferential direction about the predetermined direction A in the cross section perpendicular to the predetermined direction A, the entire length of the cartridge recess portion 130B$_3$ is preferably longer than the width of the inhaler through hole 110B. It is noted that FIG. 8 illustrates an H-H cross section (a perpendicular cross section with respect to the predetermined direction A) illustrated in FIG. 7.

Figure 9:
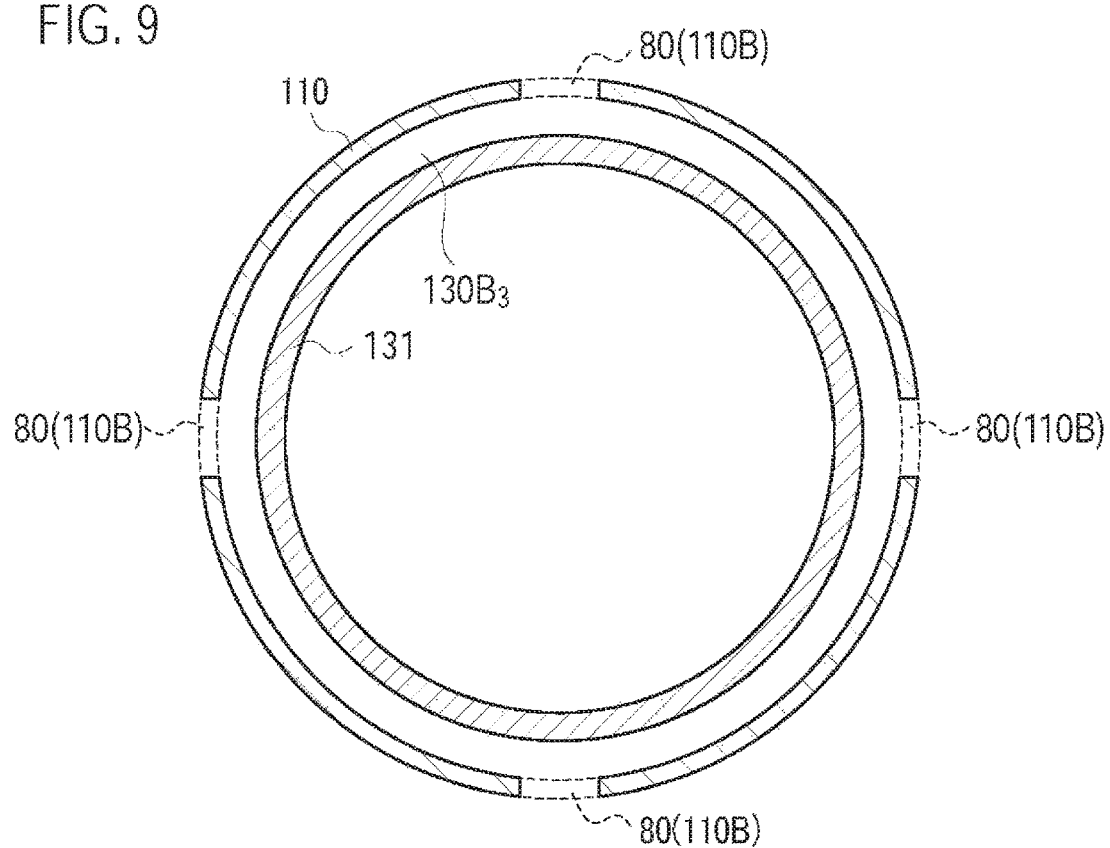
FIG. 9 is a diagram illustrating the atomizing unit 111 and the cartridge 130 according to the third modification.

Alternatively, as illustrated in FIG. 9, the cartridge recess portion 130B$_3$ may be annularly continued in the cross section perpendicular to the predetermined direction A. That is, from the inhaler through hole 110B to the outlet 130A$_1$, an outer diameter of the cartridge housing 131 may be smaller than that of another portion. It is noted that FIG. 9 illustrates the H-H cross section (the perpendicular cross section with respect to the predetermined direction A) illustrated in FIG. 7.

Here, "annularly continued" may be a state not continued, in the cross section perpendicular to the predetermined direction A, over the entire length in the circumferential direction (360°) around the predetermined direction A. For example, the cartridge recess portion 130B$_3$ may be partitioned by discontinuous portions in the circumferential direction. It is noted that, in the circumferential direction, it may be sufficient that each width of the cartridge recess portion 130B$_3$ partitioned by the discontinuous portions is wider than the interval between the inhaler through holes 110B adjacent to each other (the closest interval). Alternatively, in the circumferential direction, it may be sufficient that the width of the inhaler through hole 110B is wider than the width of the discontinuous portions.

In addition, it may be sufficient that the cartridge recess portion 130B$_3$ includes a portion having an annularly continued shape at a position (i.e., the H-H cross section) where the inhaler through hole 110B is provided in the predetermined direction A, as illustrated in FIG. 9. Therefore, the cartridge recess portion 130B$_3$ may have the cross section illustrated in FIG. 8 (an aspect in which the inhaler through hole 110B does not exist and the inhaler main unit 110 is annularly continued) at a position (for example, a G-G cross section) toward the downstream from the position at which the inhaler through hole 110B is provided in the predetermined direction A. As a result, the second air flow path can be always formed without paying attention to the relative portion of the cartridge housing 131 and the inhaler housing 110X in the rotation direction of the cartridge housing 131. Furthermore, even if the inhaler housing 110X is formed by a flexible member, the inhaler housing 110X is not easily crushed, upon the user pushing the inhaler housing 110X at the position (for example, the G-G cross section) toward the downstream from the position at which the inhaler through hole 110B is provided in the predetermined direction A.

It is noted that in the third modification, the second air flow path is formed by the inlet 80 (inhaler through hole 110B), the cartridge recess portion 130B$_3$, and the outlet 130A$_1$. That is, the second air flow path does not include the aerosol flow path (the internal space of the cartridge housing 131).

In the third modification, the cartridge recess portion 130B₃ is configured by reducing the thickness of the cartridge housing 131. However, the third modification is not limited thereto. It may be sufficient that the cartridge recess portion 130B₃ is configured such that the space is formed between the inside surface of the inhaler housing 110X and the outside surface of the cartridge housing 131. For example, the cartridge housing 131 has a fixed thickness and has a recess portion internally recessed in the cross section perpendicular to the predetermined direction A, and such recess portion may be employed as the cartridge recess portion 130B₃.

In the third modification, the amount of air flowing in from the inlet 80 (inhaler through hole 110B) is equal to or more than 50% of the amount of air flowing out from the outlets (the outlet 130A and the outlet 130A₁). Therefore, even if the air flowing in from the inlet 112A passes through the atomizer 111R, the resistance-to-draw of the entire air flow path can be easily suppressed to 25 mmAq or less.

(Operation and Effect)

In the third modification, the second air flow path does not include a part of the air flow path (the internal space of the cartridge housing 131). In other words, the flavor source 132 does not exist within the second air flow path. Therefore, the resistance-to-draw of the entire air flow path can be further easily suppressed to 25 mmAq or less.

In the third modification, if the cartridge recess portion 130B₃ is annularly continued in the cross section perpendicular to the predetermined direction A, even if the cartridge housing 131 is inserted into the inhaler housing 110X without paying attention to the relative position of the cartridge housing 131 and the inhaler housing 110X in the rotation direction of the cartridge housing 131, the inhaler through hole 110B communicates with the cartridge recess portion 130B₃, and thus, the second air flow path can be always formed.

[Fourth Modification]

A fourth modification of the first embodiment will be described, below. Differences from the first modification will be mainly described, below.

In the first modification, the inlet 80 (second inlet) is provided on the inhaler housing 110X at a position where the inhaler housing 110X and the cartridge housing 131 are overlapped. However, in the fourth modification, the inlet 80 (second inlet) is provided on the cartridge housing 131 at a position where the inhaler housing 110X and the cartridge housing 131 are not overlapped.

Figure 10:
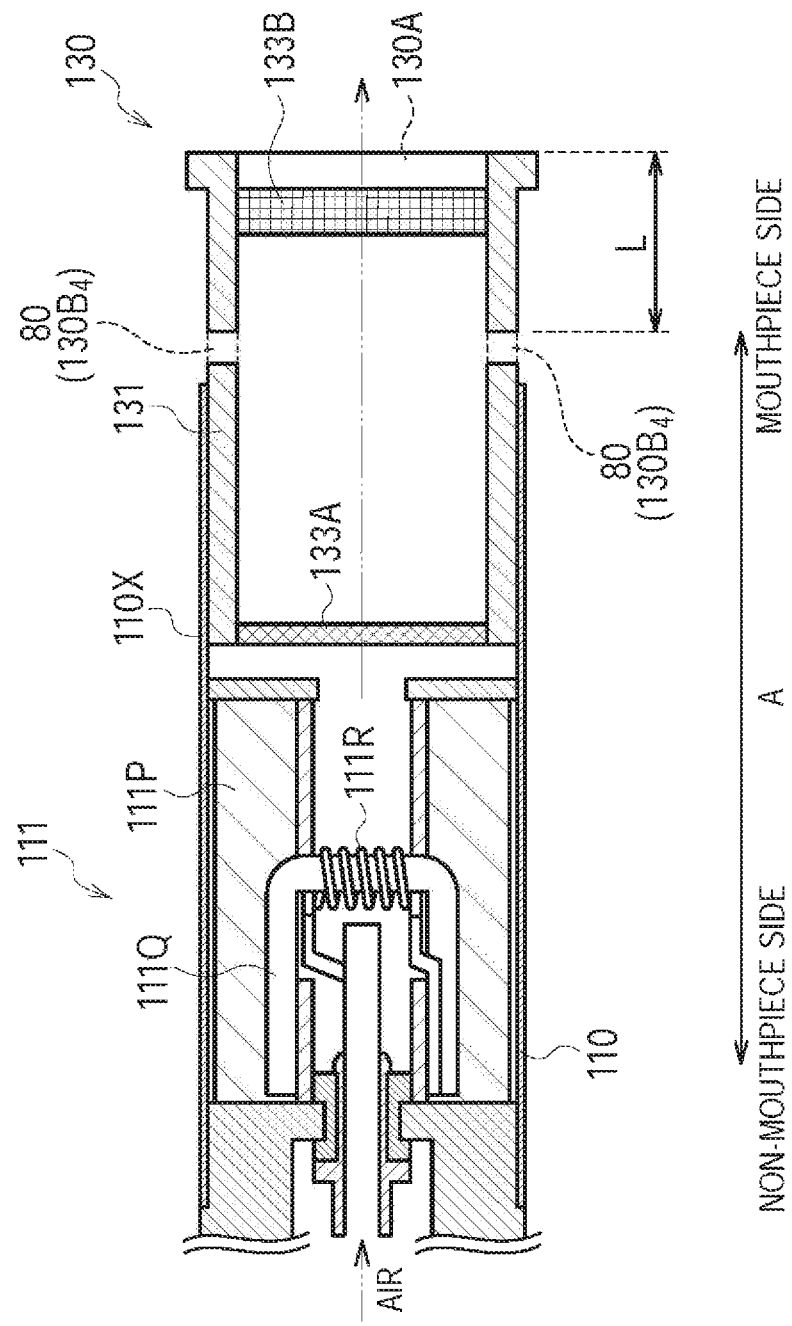
FIG. 10 is a diagram illustrating the atomizing unit 111 and the cartridge 130 according to a fourth modification.

Specifically, the cartridge housing 131 is configured to be inserted along the predetermined direction A into the inhaler housing 110X. As illustrated in FIG. 10, the cartridge housing 131 has a cartridge through hole 130B₄ penetrating the cartridge housing 131. The cartridge through hole 130B₄ is provided at an exposed portion exposed from the inhaler housing 110X. The cartridge through hole 130B₄ forms the inlet 80 (second inlet). In other words, the cartridge housing 131 includes a cartridge protruding portion (exposed portion) extending toward the outlet 130A side from the inhaler housing 110X in the predetermined direction A. The cartridge through hole 130B₄ (second inlet) is provided at the cartridge protruding portion (exposed portion) of the cartridge housing 131.

It is noted that in the fourth modification, the cartridge housing 131 includes the protruding portion extending toward the outlet 130A side from the inhaler housing 110X in the predetermined direction A; however, the fourth modification is not limited thereto. For example, the inhaler housing 110X may include an inhaler protruding portion extending toward the outlet 130A side from the cartridge housing 131 in the predetermined direction A. In such a case, the above-described inlet 80 may be provided at the inhaler protruding portion of the inhaler housing 110X.

(Operation and Effect)

In the fourth modification, the cartridge housing 131 has the inlet 80 (second inlet) at the exposed portion exposed from the inhaler housing 110X. Therefore, in addition to a similar effect to that of the first modification, even if the cartridge housing 131 is inserted into the inhaler housing 110X without paying attention to the relative position of the cartridge housing 131 and the inhaler housing 110X in the rotation direction of the cartridge housing 131, the second air flow path can be always formed.

[Fifth Modification]

A fifth modification of the first embodiment will be described, below. Differences from the first embodiment will be mainly described, below.

Specifically, in the first embodiment, the inhalation switch 51 is connected to the sensor 20, and operates based on the response value output from the sensor 20. In the fifth modification, the inhalation switch 51 is connected to an inhalation button (for example, the push button 30), and operates based on an operation on the inhalation button. The inhalation button is an example of an operation interface operated by the user. The fifth modification does not require the above-described sensor 20.

In the fifth modification, the inhalation button is an operation interface configured to be depressed during a period the user performs the inhaling action. That is, the inhalation switch 51 is switched to the ON state if the inhalation button is depressed, and is switched to the OFF state if the inhalation button is not depressed.

It is noted that the position of the inhalation button (for example, the push button 30) is not particularly limited. As illustrated in FIG. 1, the inhalation button may be provided at the non-mouthpiece end of the inhaler housing 110X or may be provided on an outer circumference of the inhaler housing 110X (for example, the second cylinder 112X of the electrical unit 112).

[Sixth Modification]

A sixth modification of the first embodiment will be described, below. Differences from the fourth modification will be mainly described, below.

In the fourth modification, the cartridge through hole 130B₄ forms the inlet 80 (second inlet) and is provided on the mesh 133A side relative to the filter 133B. However, in the sixth modification, the cartridge through hole 130B₄ forms the inlet 80 (second inlet) and is provided on the outlet 130A side relative to the flavor source 132.

Figure 11:
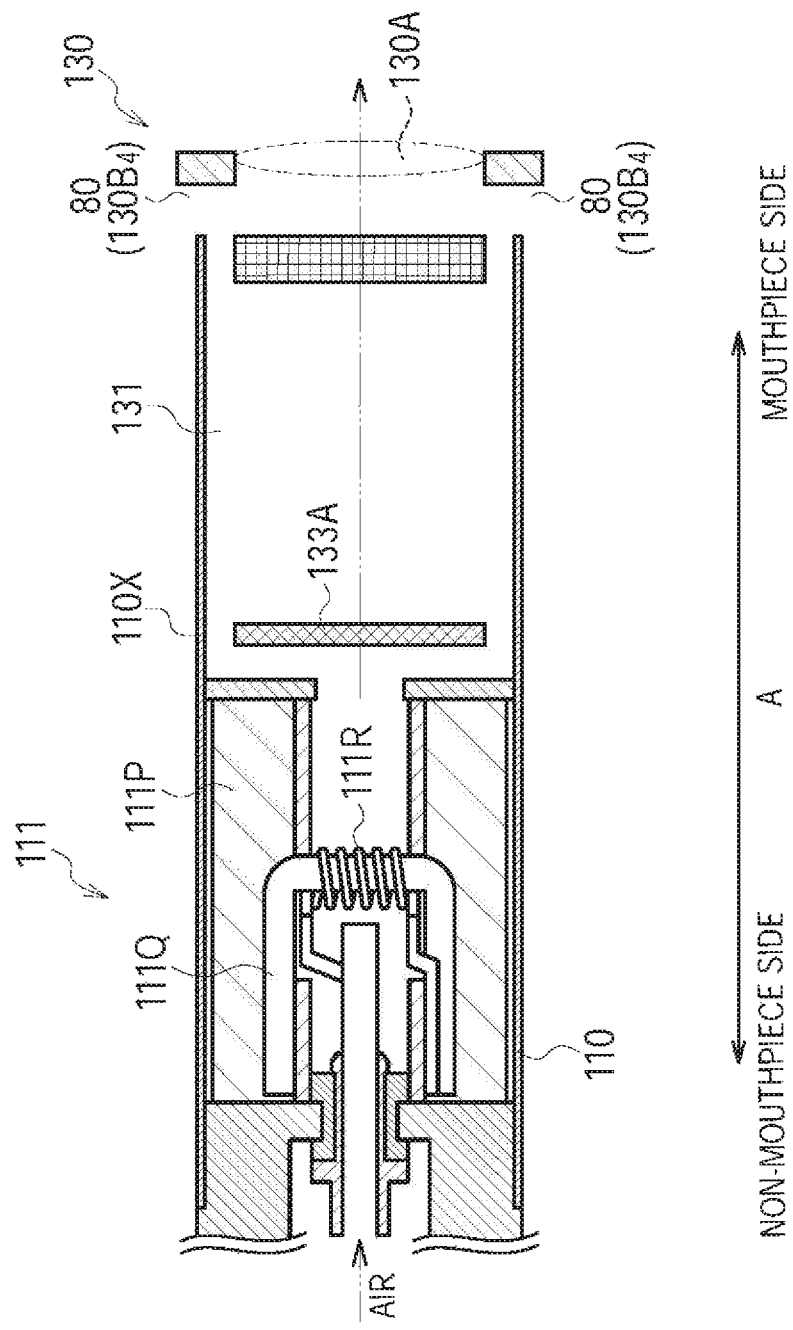
FIG. 11 is a diagram illustrating the atomizing unit 111 and the cartridge 130 according to a sixth modification.

Specifically, as illustrated in FIG. 11, the cartridge housing 131 has the cartridge through hole 130B₄ penetrating the cartridge housing 131. The cartridge through hole 130B₄ is provided on the outlet 130A side relative to the flavor source 132. The cartridge through hole 130B₄ is provided on the outlet 130A side relative to the filter 133B. The cartridge through hole 130B₄ may be provided at a position overlapping with the filter 133B.

In the sixth modification, the inlet 80 (second inlet) provided on the outlet 130A side relative to the flavor source 132 is illustrated as the cartridge through hole 130B₄. However, the embodiment is not limited thereto. The inlet 80 (second inlet) provided at the above-described position may be the inhaler through hole 110B provided on the inhaler main unit 110. Alternatively, the inlet 80 (second inlet) provided at the above-described position may be the inhaler through hole 110B and the cartridge through hole 130B.

[Seventh Modification]

A seventh modification of the first embodiment will be described, below. Differences from the first modification will be mainly described, below.

In the first modification, the flavor inhaler 100 has the cartridge 130. However, in the seventh modification, the flavor inhaler 100 does not have the cartridge 130.

Figure 12:
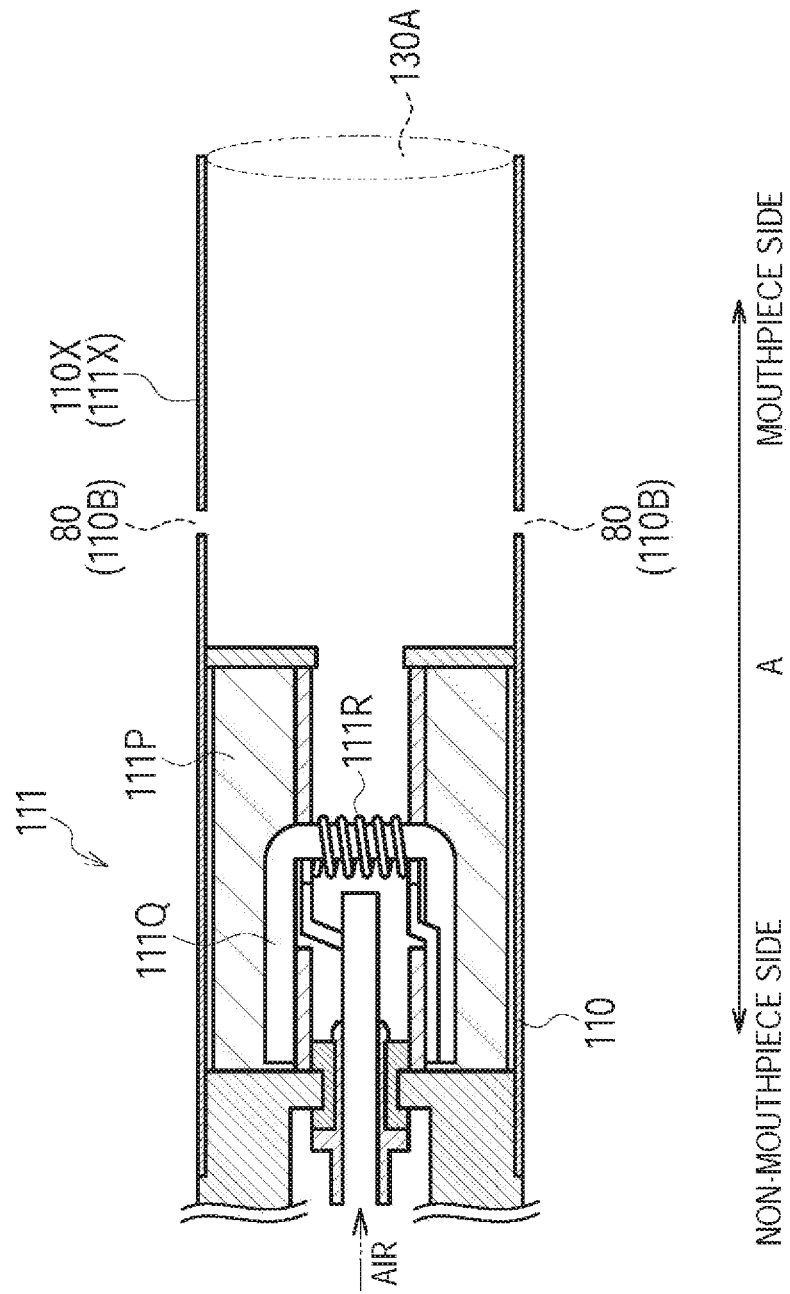
FIG. 12 is a diagram illustrating the atomizing unit 111 and the cartridge 130 according to a seventh modification.

Specifically, as illustrated in FIG. 12, the flavor inhaler 100 does not have the cartridge 130. Similarly to the first modification, the inhaler housing 110X may have the inhaler through hole 110B forming the inlet 80 (second inlet). That is, the non-burning type flavor inhaler 100 may have the second air flow path not passing through the atomizer 111R, in addition to the first air flow path passing through the atomizer 111R.

However, the seventh modification is not limited thereto. The inhaler housing 110X may not need to have the inhaler through hole 110B forming the inlet 80 (second inlet). That is, the non-burning type flavor inhaler 100 may not need to have the second air flow path not passing through the atomizer 111R.

[Eighth Modification]

An eighth modification of the first embodiment will be described, below. Differences from the first embodiment will be mainly described, below. In the eighth modification, an example of the sensor 20 for detecting the inhaling action of the user will be described.

As described above, the inhaler housing 110X has the first cylinder 111X (first housing) that houses the atomizer 111R, and the second cylinder 112X (second housing), removable from the first cylinder 111X, that houses the power source 10. The sensor 20 is housed in the second cylinder 112X and is provided on the first cylinder 111X side relative to the power source 10. That is, the sensor 20 is provided in the vicinity of a site where the second cylinder 112X is connected to the first cylinder 111X (the inlet 112A in the eighth modification).

Figure 13:
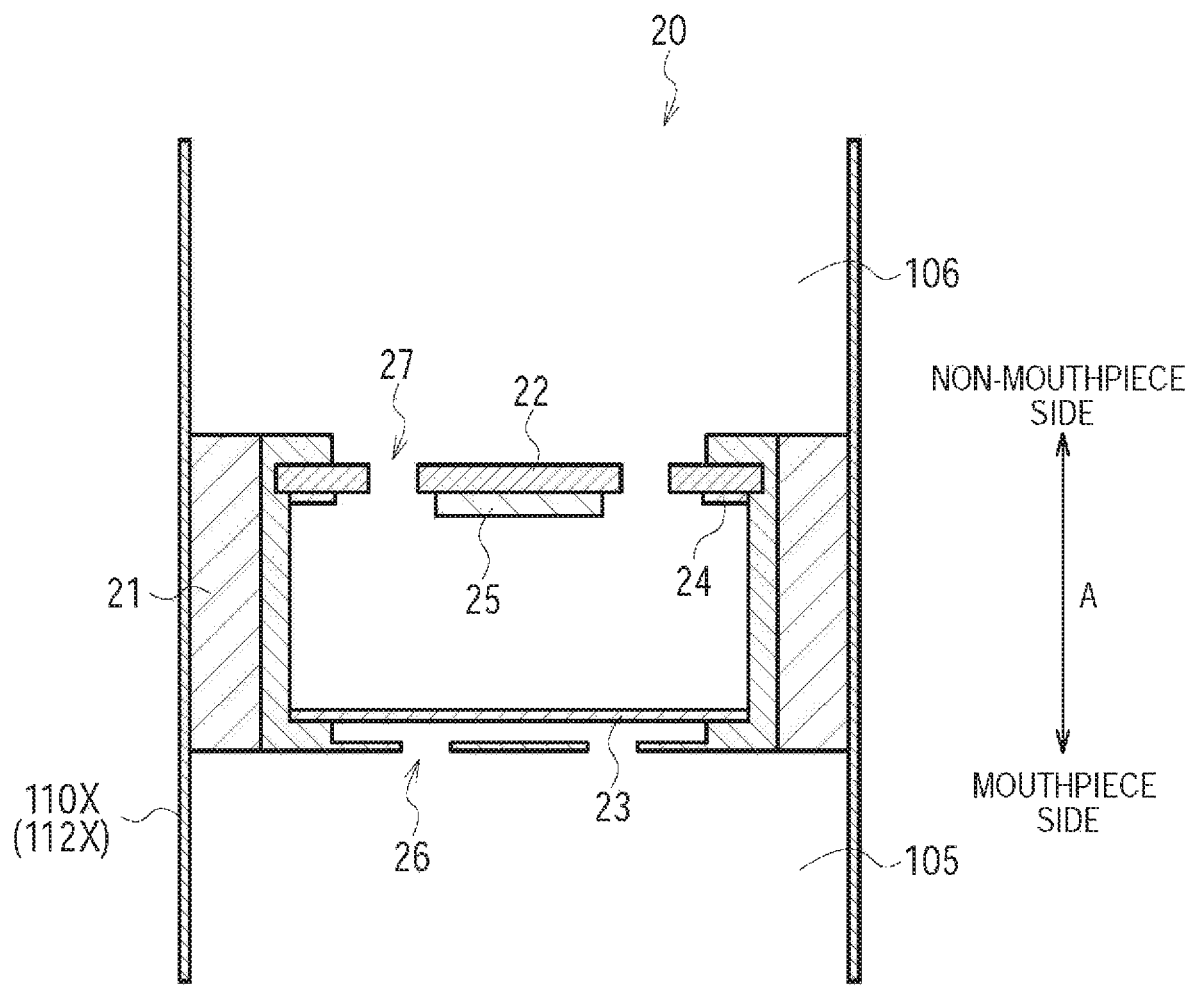
FIG. 13 is a diagram illustrating a sensor 20 according to an eighth modification.

As illustrated in FIG. 13, the inhaler housing 110X (here, the second cylinder 112X) has a first hollow 105 provided at a side same with the inlet 112A and the outlet 130A relative to the sensor 20, and a second hollow 106 provided at the opposite side of the inlet 112A and the outlet 130A relative to the sensor.

Under such an assumption, the sensor 20 is a sensor having a capacitor and outputs a response value (for example, a voltage value) indicating the electric capacitance of the capacitor corresponding to the differential pressure between the internal pressure of the first hollow 105 and the internal pressure of the second hollow 106, for example. As illustrated in FIG. 13, the sensor 20 has a cover 21, a substrate 22, an electrode film 23, a fixed electrode 24, a control circuit 25, an opening 26, and an opening 27. There is no gap between the cover 21 and the inhaler housing 110X, and the first hollow 105 and the second hollow 106 are partitioned by the sensor 20 not to communicate with each other within the inhaler housing 110X. The substrate 22 is provided with the fixed electrode 24 and the control circuit 25. The electrode film 23 deforms depending on change in the differential pressure between the internal pressure of the first hollow 105 and the internal pressure of the second hollow 106. The fixed electrode 24 forms the electrode film 23 and a capacitor. The electric capacitance of the capacitor changes depending on the deformation of the electrode film 23. The control circuit 25 detects the electric capacitance that changes in accordance with the deformation of the electrode film 23, and outputs a response value based on the detected change of the electric capacitance. The opening 26 communicates with the first hollow 105. Therefore, if the internal pressure of the first hollow 105 changes due to the inhaling action, then the electrode film 23 deforms.

Specifically, for example, if the inhaling action is performed, the internal pressure of the first hollow 105 is reduced whereas the internal pressure of the second hollow 106 does not substantially change and is almost equal to the atmospheric pressure, and thus, the sensor 20 substantially detects the pressure change in the first hollow 105. In addition, for example, if a blowing action is performed, the internal pressure of the first hollow 105 is increased whereas the internal pressure of the second hollow 106 does not substantially change and is almost equal to the atmospheric pressure, and thus, the sensor 20 substantially detects the pressure change in the first hollow 105.

It is noted that in the eighth modification, the inlet 112A is provided between the sensor 20 and the atomizer 111R. For example, a distance between the inlet 112A and the sensor 20 may be 20 mm or less. The distance between the inlet 112A and the sensor 20 is preferably 15 mm or less, and more preferably 10 mm or less. The second hollow is opened to the atmosphere. For example, the second hollow may communicate with an opening of the non-mouthpiece end of the second cylinder 112X via the gap between the power source 10 and the second cylinder 112X, or may communicate with a hole provided on the side surface of the second cylinder 112X.

(Operation and Effect)

In the eighth modification, the sensor 20 is housed in the second cylinder 112X and is provided on the first cylinder 111X side relative to the power source 10. That is, the sensor 20 is provided in the vicinity of a site where the second cylinder 112X is connected to the first cylinder 111X (the inlet 112A in the eighth modification). Therefore, even if the resistance-to-draw of the entire air flow path is low, such as 25 mmAq or less, the accuracy for detecting the inhaling action is improved.

In the eighth modification, the first hollow 105 and the second hollow 106 are partitioned by the sensor 20 not to communicate with each other within the inhaler housing 110X. With such configuration, the internal pressure of the first hollow 105 is likely to become higher in accordance with the inhaling action, and thus, even if the resistance-to-draw of the entire air flow path is low, such as 25 mmAq or less, the accuracy for detecting the inhaling action is improved.

[Ninth Modification]

Figure 14:
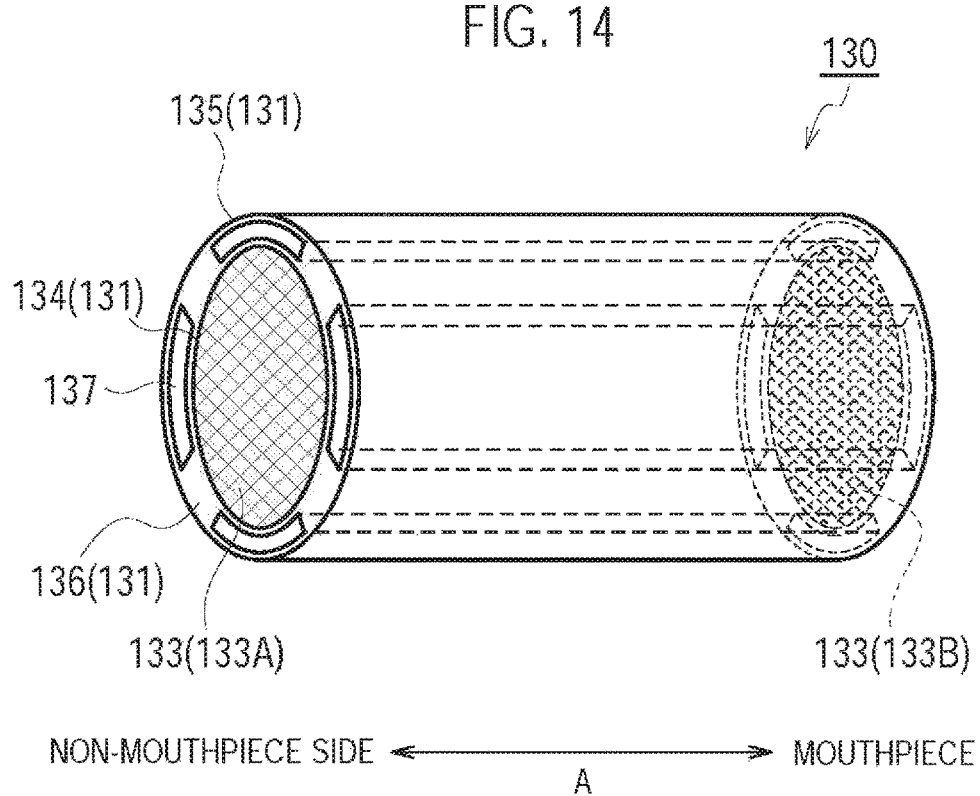
FIG. 14 is a drawing illustrating the cartridge 130 according to a ninth modification.
Figure 15:
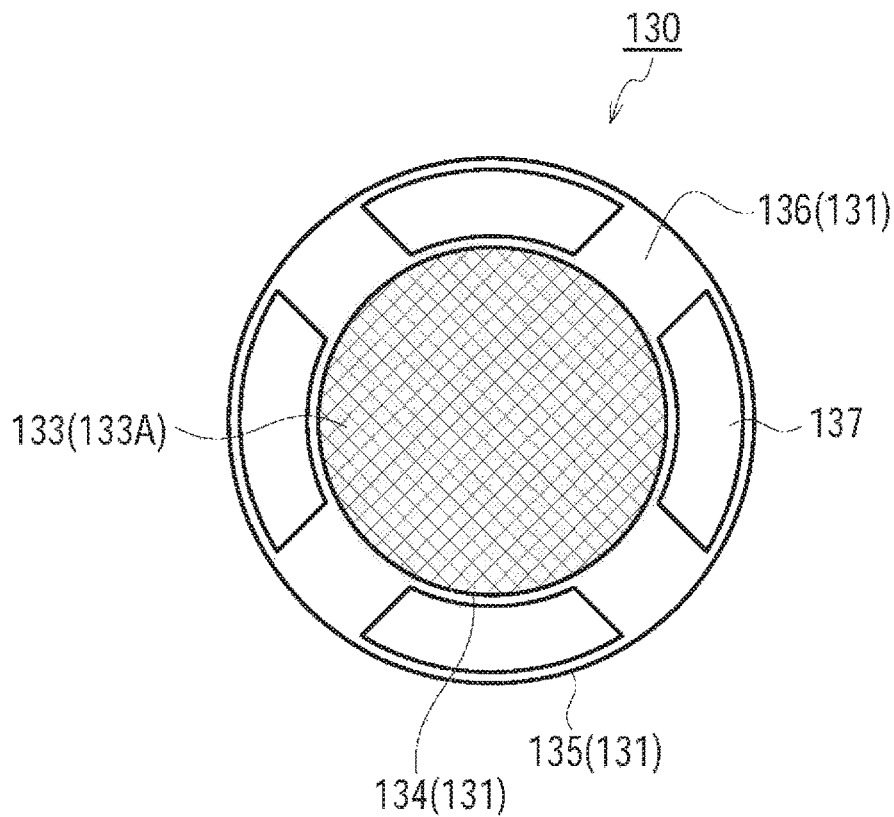
FIG. 15 is a diagram illustrating the cartridge 130 according to the ninth modification.

A ninth modification of the first embodiment will be described, below. Differences from the first embodiment will be mainly described, below. In the ninth modification, modifications of the above-described atomizing unit 111 and cartridge 130 will be described. FIG. 14 is a perspective view of the cartridge 130 according to the ninth modification, and FIG. 15 is a diagram of the cartridge 130 according to the ninth modification viewed from the mouthpiece side. FIG. 16 is a cross-sectional schematic view illustrating an internal structure of the flavor inhaler 100 with the cartridge 130 being housed in the inhaler housing 110X.

Specifically, in the ninth modification, the aerosol flow path forming a part of the air flow path includes: a first aerosol flow path 140A configured to lead the aerosol toward the outlet 130A side through the flavor source 132; and a second aerosol flow path 140B different from the first aerosol flow path 140A. The reduction ratio of aerosol in the second aerosol flow path 140B is smaller than the reduction ratio of aerosol in the first aerosol flow path 140A. Furthermore, the amount of aerosol being led toward the mouthpiece side through the second aerosol flow path 140B is preferably equal to or more than the amount of aerosol being led toward the mouthpiece side through the first aerosol flow path 140A. Here, the "reduction ratio" refers to the ratio of "aerosol amount lost in flow path (flow-in amount−flow-out amount)" to "aerosol amount flowing into flow path (flow-in amount)" (i.e., (flow-in amount−flow-out amount)/flow-in amount).

Here, both of the first aerosol flow path 140A and the second aerosol flow path 140B are formed inside the cartridge housing 131. In other words, the first aerosol flow path 140A formed in the cartridge housing 131 and the second aerosol flow path 140B formed in the cartridge housing 131 are separately formed not to cross each other. For example, the second aerosol flow path 140B is a flow path configured to lead the aerosol toward the outlet 130A side without passing through the flavor source 132.

In particular, as illustrated in FIG. 14 and FIG. 15, the cartridge 130 has, as the above-described cartridge housing 131, an inner body 134, an outer body 135, and a rib 136. It should be noted that in FIG. 14, the above-described flavor source 132 is omitted.

The inner body 134 has a tubular shape extending along the predetermined direction A. The inner body 134 houses the flavor source 132. The mesh 133A is provided at the non-mouthpiece side of the inner body 134, and the filter 133B is provided at the mouthpiece side of the inner body 134.

The outer body 135 has a tubular shape extending along the predetermined direction A. The outer body 135 houses the inner body 134. The outer body 135 is fixed to the inner body 134 by the rib 136 extending along the predetermined direction A.

In the ninth modification, the outer body 135 is fixed to the inner body 134 by four ribs 136, and a space 137 extending along the predetermined direction A is formed between the ribs 136 adjacent to each other.

As illustrated in FIG. 16, in a case where the cartridge 130 according to the ninth modification is employed, the above-described first aerosol flow path 140A is a flow path passing through an inner side of the inner body 134, and the above-described second aerosol flow path 140B is a flow path passing through the space 137.

In the ninth modification, a case is illustrated where the cartridge housing 131 is formed by the inner body 134, the outer body 135, and the rib 136. However, the ninth modification is not limited thereto. It should be noted that various modifications can be applied as long as both of the first aerosol flow path 140A and the second aerosol flow path 140B are formed inside the cartridge housing 131.

In the ninth modification, both of the first aerosol flow path 140A and the second aerosol flow path 140B are formed mainly inside the cartridge housing 131, and similarly to the first embodiment, a branch part 145 of the first aerosol flow path 140A and the second aerosol flow path 140B is provided outside the cartridge housing 131.

It is noted that the first aerosol flow path 140A and the second aerosol flow path 140B have a common flow path common to each other. The above-described branch part 145 is provided in the common flow path formed between the atomizing unit 111 and the cartridge 130. Furthermore, two or more common parts may be provided. In other words, the first aerosol flow path 140A and the second aerosol flow path 140B may meet or branch at two or more points.

In the ninth modification, at least a part of the first aerosol flow path 140A is formed by the inhaler housing 110X and the cartridge housing 131. At least a part of the second aerosol flow path 140B is formed by the inhaler housing 110X and the cartridge housing 131.

(Operation and Effect)

In the ninth modification, the resistance-to-draw of the entire air flow path can be easily suppressed to 25 mmAq or less by providing the second aerosol flow path 140B separately from the first aerosol flow path 140A. Since the reduction ratio of aerosol in the second aerosol flow path 140B is smaller than the reduction ratio of aerosol in the first aerosol flow path 140A, the influence in which the aerosol is filtered by the flavor source 132 is small, and thus, the aerosol loss can be suppressed. Furthermore, since the second aerosol flow path 140B is a flow path configured to lead the aerosol toward the outlet 130A side without passing through the flavor source 132, the aerosol is not filtered by the flavor source 132, and thus, the aerosol loss can be suppressed.

In the ninth modification, the first aerosol flow path 140A and the second aerosol flow path 140B are formed inside the cartridge housing 131. Therefore, the second aerosol flow path 140B can be formed without changing the design of the inhaler main unit 110.

[Tenth Modification]

A tenth modification of the first embodiment will be described, below. Differences from the first embodiment will be mainly described, below. In the tenth modification, modifications of the above-described atomizing unit 111 and cartridge 130 will be described.

Figure 17A:
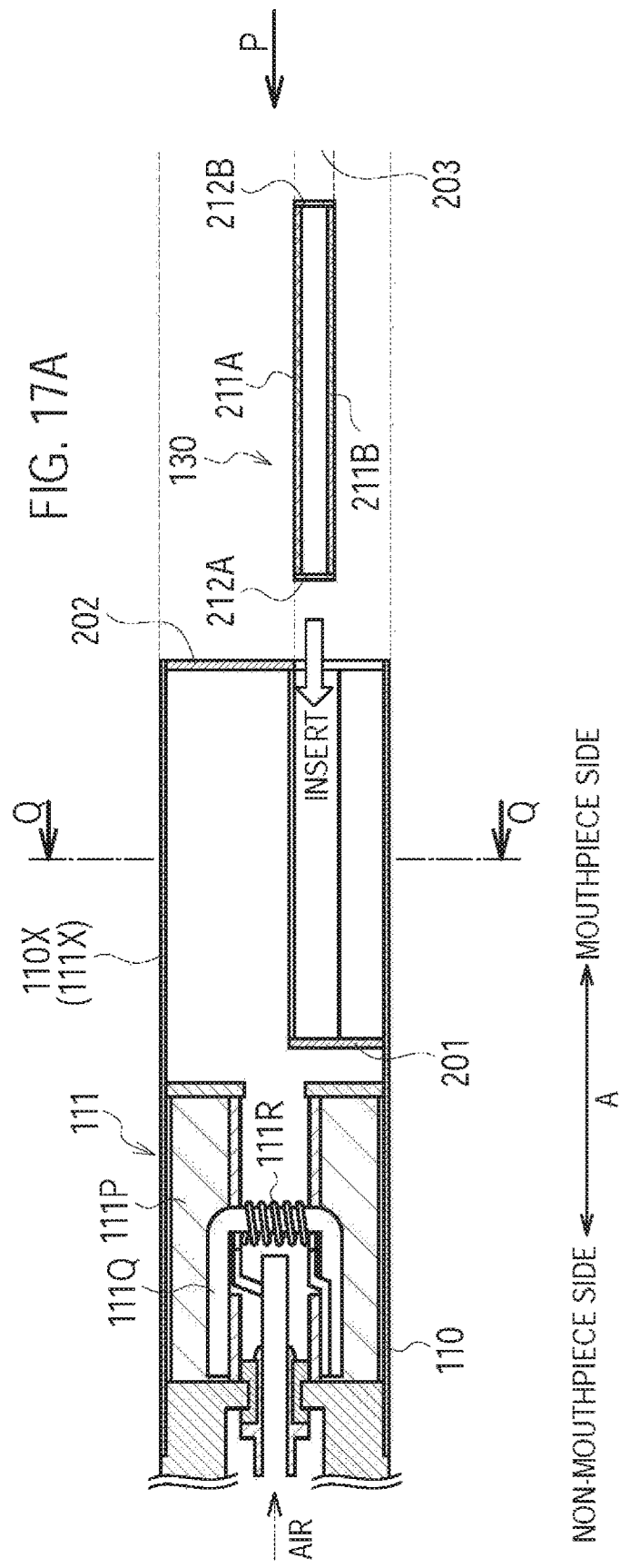
FIGS. 17A-17C are diagrams illustrating the atomizing unit 111 and the cartridge 130 according to a tenth modification.
Figure 17C:
Figure 17B:
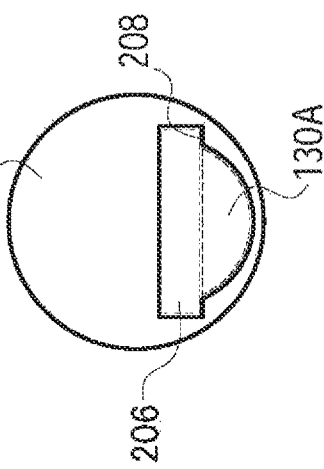
Figure 18A:
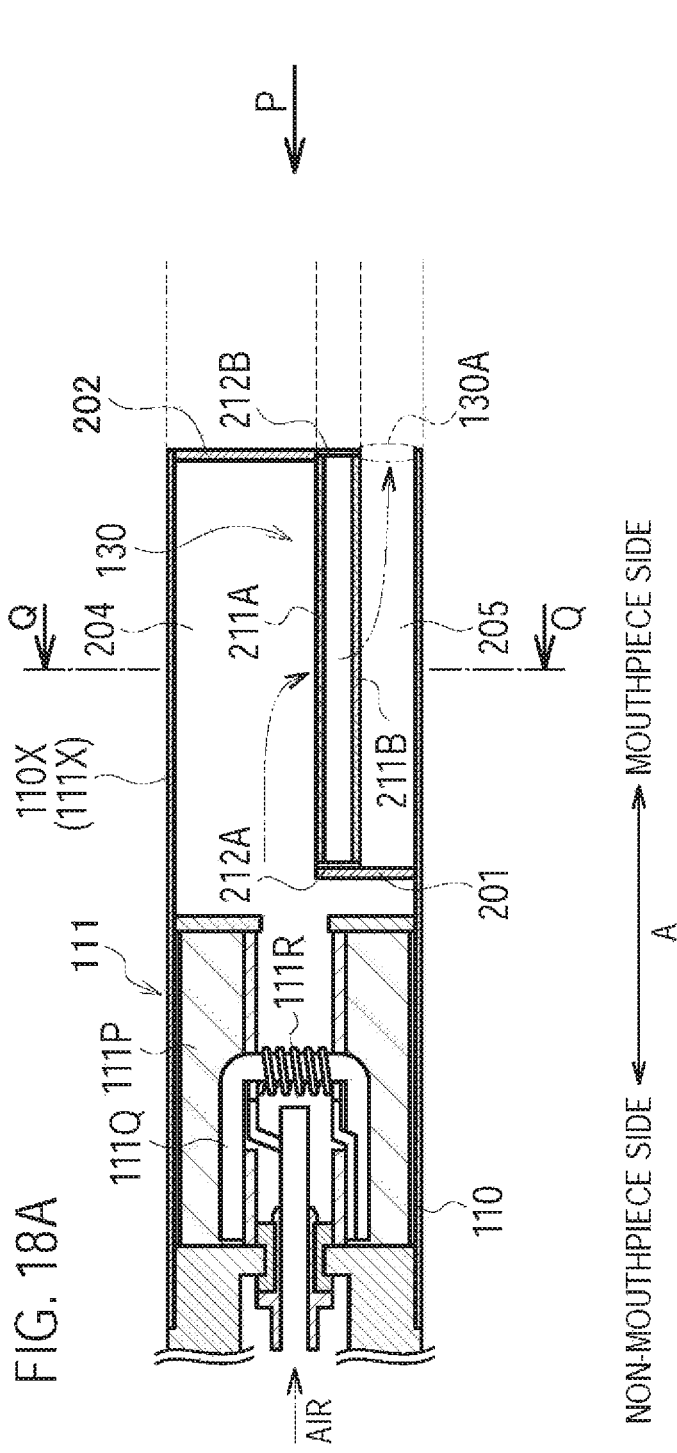
FIGS. 18A-18C are diagrams illustrating the atomizing unit 111 and the cartridge 130 according to the tenth modification.
Figure 18C:
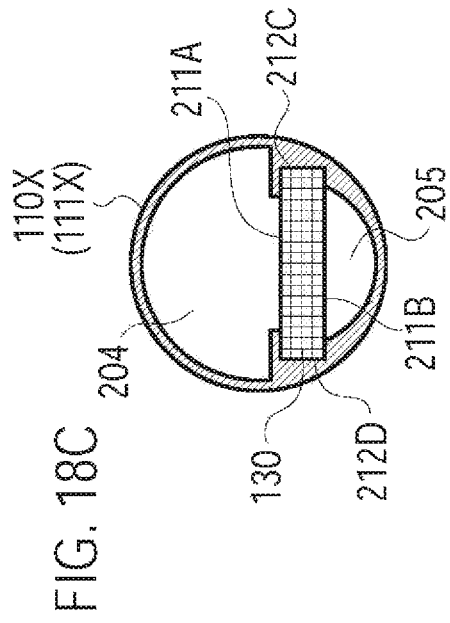
Figure 18B:
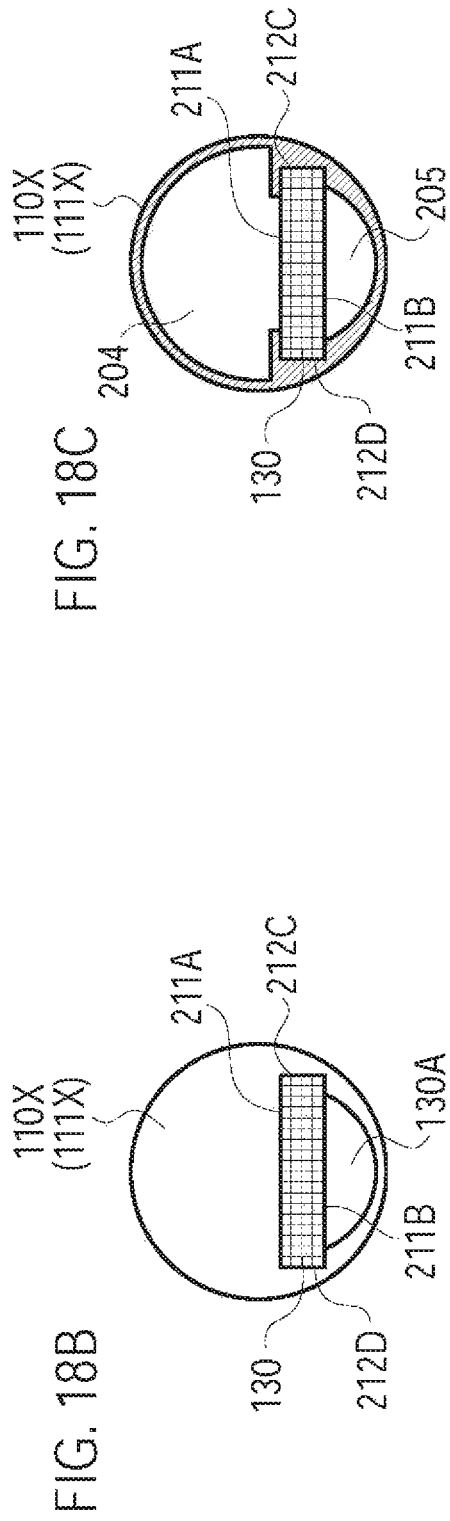

Specifically, as illustrated in FIG. 17 and FIG. 18, the flavor inhaler 100 has the cartridge 130 including the flavor source 132 (flavor source unit) provided on the outlet 130A side relative to the atomizer 111R. The inhaler housing 110X has a shape extending along the predetermined direction A, and has a wall body 201 holding the cartridge 130, a wall body holder 202, a regulation part 208, and a regulation part 209. It is noted that FIG. 17(B) is a side view of the flavor inhaler 100 viewed from the P side illustrated in FIG. 17(A), and FIG. 17(B) is a Q-Q cross section of the FIG. 17(A). Similarly, FIG. 18(B) is a side view of the flavor inhaler 100 viewed from the P side illustrated in FIG. 18(A), and FIG. 18(B) is a Q-Q cross section of FIG. 18(A).

As illustrated in FIG. 17, the cartridge 130 is inserted into an insertion opening 206 provided on the inhaler housing 110X along the predetermined direction A. As illustrated in FIG. 18, the cartridge 130 is held by the inhaler housing 110X.

Here, the wall body 201 has a function of regulating an insertion length of the cartridge 130, and a wall body 202 has a function of partitioning a first space 204. The regulation part 208 is continued from the wall body 202 side to the wall body 201 along the predetermined direction A, and supports a lower surface of the cartridge 130 (wall body 211B). The regulation part 209 is continued from the wall body 202 side to the wall body 201 along the predetermined direction A, and supports an upper surface of the cartridge 130 (wall body 211A). Thus, in a vertical direction in FIG. 18, the movement of the cartridge 130 is controlled by the regulation part 208 and the regulation part 209.

Here, the cartridge 130 is arranged within the inhaler housing 110X to partition the aerosol flow path that is a flow path of aerosol generated from the atomizer 111R into the first space 204 at the inlet 112A side and a second space 205 at the outlet 130A side. Specifically, the cartridge 130 partitions the first space 204 and the second space 205 along the predetermined direction A.

In the tenth modification, an area of the cartridge 130 being exposed to at least any one of the first space 204 and the second space 205 is larger than a cross section area defined by an inner circumference of the inhaler housing 110X in a cross section perpendicular to a predetermined direction.

For example, the cartridge 130 has first wall bodies 211A and 211B being exposed to the first space 204 and the second space 205, and second wall bodies 212A to 212D continuing to the first wall bodies 211A and 211B. The first wall bodies 211A and 211B may include a curved portion, and the second wall bodies 212A to 212D may include a curved portion. The second wall bodies 212A to 212D may need to be exposed to neither the first space 204 nor the second space 205.

The first wall bodies 211A and 211B are formed by a member having air permeability. The first wall bodies 211A and 211B may be formed by a mesh or a filter similarly to the first embodiment, or may be formed by a nonwoven fabric, and the like. An area of an outer surface of the first wall bodies 211A and 211B is larger than an area of an outer surface of the second wall bodies 212A to 212D.

The aerosol generated from the atomizer 111R is led from the first space 204 into the cartridge 130 through the first wall body 211A, and the aerosol having led into the cartridge 130 is led into the second space 205 through the first wall body 211B.

(Operation and Effect)

In the tenth modification, the area of the outer surface of a pair of first wall bodies 211A and 211B is larger than the area of the outer surface of a pair of second wall bodies 212A and 212B. Therefore, the aerosol can be easily passed through the entire flavor source 132 and the resistance-to-draw of the entire air flow path can be easily suppressed to 25 mmAq or less. Furthermore, since the distance of aerosol passing through the flavor source 132 is shortened, the influence in which the aerosol is filtered by the flavor source 132 is small, and thus, the aerosol loss can be suppressed.

Other Embodiments

The present invention has been described in terms of the embodiments set forth above; however, the invention should not be understood to be limited by the statements and the drawings forming a part of this disclosure. From this disclosure, various alternative embodiments, examples, and operational technologies will be obvious to those skilled in the art.

Although not particularly mentioned in the embodiment, in the cartridge 130 being connected to the inhaler main unit 110, there may be a case where the inlet 80 cannot be formed if an attention is not paid to the relative position of the cartridge housing 131 and the inhaler housing 110X in the rotation direction of the cartridge housing 131 (for example, see FIG. 4 and FIG. 8). In such a case, at least one of the cartridge 130 and the inhaler main unit 110 preferably has a positioning function for forming the inlet 80. An example of such positioning function is described as follows.

For example, a case is assumed where the inhaler housing 110X forming the inhaler main unit 110 has a cylindrical shape and the cartridge 130 has a columnar shape. That is, in the cartridge 130 being inserted into the inhaler housing 110X, the cartridge 130 is rotatable about a central axis of the cartridge 130 extending along the predetermined direction A. To uniquely specify the relative position of the inhaler main unit 110 and the cartridge 130 in the rotation direction of the cartridge housing 131, a guide rib may be provided on an inner surface of the inhaler housing 110X, and a guide groove may be provided on an outer surface of the cartridge housing 131. Conversely, a guide groove may be provided on the inner surface of the inhaler housing 110X, and a guide rib may be provided on the outer surface of the cartridge housing 131. The guide groove and the guide rib preferably have a shape extending along the predetermined direction A.

Alternatively, a case is assumed where the inhaler housing 110X forming the inhaler main unit 110 has a hollow having a polygonal shape or an elliptical shape, and the cartridge 130 has a polygonal columnar shape or an elliptical columnar shape. In such a case, the inhaler housing 110X and the cartridge 130 preferably have a shape for uniquely specifying the relative position of the cartridge 130 and the inhaler main unit 110. Alternatively, the inhaler main unit 110 and the cartridge 130 may have a guide rib or a guide groove for uniquely specifying the relative position of the inhaler main unit 110 and the cartridge 130 in a direction along an outer circumference of the cartridge housing 131 in a perpendicular direction with respect to the predetermined direction A.

Alternatively, the inhaler main unit 110 and the cartridge 130 may have an indication for uniquely specifying the relative position of the inhaler main unit 110 and the cartridge 130.

The embodiment describes a feature of uniquely specifying the relative position of the cartridge housing 131 and the inhaler housing 110X in the rotation direction of the cartridge housing 131. However, the embodiment is not limited thereto. Specifically, it is preferable that the relative position of the cartridge housing 131 and the inhaler housing 110X is uniquely specified in the predetermined direction A. For example, the inhaler housing 110X preferably has a spacer for defining an insertion depth of the cartridge housing 131 to the inhaler housing 110X. The insertion depth of the cartridge housing 131 to the inhaler housing 110X is defined by the spacer, and thus, the relative position of the cartridge housing 131 and the inhaler housing 110X can be uniquely specified in the predetermined direction A.

Although not particularly mentioned in the embodiment, the controller 53 may stop the output of the power source output to the atomizer 111R even if the inhaling action is continued if a predetermined time elapses after starting the output of the power source output to the atomizer 111R. The predetermined period is shorter than an upper limit value of a standard puff period that is derived from statistics of puff periods of users. In other words, in order to suppress a situation where the stagnation and condensation of the aerosol within the aerosol flow path occurs after the inhaling action ends, it is preferable to stop the output of the power source output to the atomizer 111R during the inhaling action being performed. As a result, the aerosol loss is suppressed.

It is noted that, the standard puff period may be derived from statistics of puff periods of users, and is a period between the lower limit value of puff periods of a plurality of users and the upper limit value of puff periods of a plurality of users. The lower limit value and the upper limit value are derived based on a distribution of puff period data of users. For example, a lower limit value and an upper limit value of a 95% confidence interval of the average value may be used to derive the lower limit value and the upper limit value, or the lower limit value and the upper limit value may be derived by m±nσ (where, m is an average value, σ is a standard deviation, and n is a positive real number).

For example, the predetermined period is from one second to three seconds. By the predetermined period being one second or more, the energization time of the atomizer is not too short compared to the puff period, and therefore discomfort that is imparted to the user is mitigated. Meanwhile, by the predetermined period being three seconds or less, it is possible to set the inhalataion action in which the energization time of the atomizer is fixed to the predetermined period, to a certain number or more. Furthermore, the predetermined period may be 1.5 seconds or more and 2.5 seconds or less. As a result, it is possible to further mitigate discomfort that is imparted to the user, and increase the inhalataion action in which the energization time of the atomizer is fixed to the predetermined period.

In the embodiment, the cartridge 130 does not include the atomizing unit 111; however, the embodiment is not limited thereto. For example, the cartridge 130 and the atomizing unit 111 may be configured as one unit.

Although not particularly mentioned in the embodiment, the atomizing unit 111 may be capable of connecting to the inhaler main unit 110.

In the embodiment, the non-burning type flavor inhaler 100 having an atomizer configured to atomize, without burning, an aerosol source by using the power has been described as an example of a flavor inhaler. However, the embodiment is not limited thereto, and other embodiments can be applied as long as the aerosol source is atomized without burning the aerosol source. For example, an example of atomizer includes an atomizer configured to generate an aerosol by using combustion heat of carbon heat source, heat generated by a chemical reaction, or other factor other than heat such as vibration.

In the embodiment, the push button 30 is provided; however, the push button 30 may not need to be provided. Furthermore, the above-described power source switch 52 may not need to be provided. That is, the power may be always supplied from the power source 10 to the sensor 20 and the control circuit 50.

In the embodiment, the cartridge 130 is provided; however, the cartridge 130 may not need to be provided. In such a case, the aerosol source preferably contains a flavor component.

In the embodiment, the flavor source unit is the cartridge 130 having the flavor source 132 within a space formed by the cartridge housing 131, the mesh 133A, and the filter 133B. However, the embodiment is not limited thereto. Specifically, the flavor source unit may be a unit (a pouch, for example) that houses shredded tobacco or a granular tobacco raw material into a bag-shaped member. Furthermore, the flavor source unit may be a unit (sheet-like member) configured to sandwich a granular tobacco raw material and a binder by a nonwoven fabric. The nonwoven fabric is formed in a sheet shape by thermal fusion bonding.

Although not particularly mentioned in the embodiment, the flavor inhaler 100 may be configured such that the resistance-to-draw of the entire air flow path is changeable to 25 mmAq or less. The "resistance-to-draw of the entire air flow path is changeable" may mean that the resistance-to-draw is changeable from above 25 mmAq to 25 mmAq or less, or may mean that a change in reverse direction is also possible. The "resistance-to-draw of the entire air flow path is changeable" may mean that the resistance-to-draw is changeable under a condition where the resistance-to-draw is 25 mmAq or less. For example, in a case illustrated in FIG. 4, the resistance-to-draw of the entire air flow path may be changed by changing an overlapping area of the inhaler through hole 110B and the cartridge through hole 130B in accordance with the pivot of the cartridge housing 131 within the inhaler main unit 110. Alternatively, the resistance-to-draw of the entire air flow path may be changed by selectively using the cartridge 130 with the cartridge through holes 130B having different sizes. The resistance-to-draw of the entire air flow path may be changed by selectively using the cartridge 130 having the cartridge through hole 130B and the cartridge 130 not having the cartridge through hole 130B. Alternatively, if the housing of the flavor inhaler 100 includes the mouthpiece as a separate member, the resistance-to-draw of the entire air flow path may be changed by selectively using mouthpieces.

Although not particularly mentioned in the embodiment, if the power is supplied from the power source 10 to the atomizer 111R for three seconds, the amount of aerosol generated from the atomizer 111R is preferably 10 mg or less.

Although not particularly mentioned in the embodiment, the outer diameter of the inhaler housing 110X is preferably 18 mm or less, and more preferably 15 mm or less.

Although not particularly mentioned in the embodiment, the capacity of battery forming the power source 10 is preferably 1000 mAh or less, and more preferably 800 mAh or less.

Although not particularly mentioned in the embodiment, a diameter of the aerosol flow path provided in the atomizing unit 111 (i.e., a diameter of a flow path interposed by a reservoir 111P) is preferably 3 mm or less.

[Experiment Result]

In an experiment, a mouthpiece sample in which an acetate filter was inserted into a polypropylene (PP) tube was prepared and 10 subjects (adult male smokers) performed an inhaling action by using the sample. Specifically, samples prepared include a sample with the resistance-to-draw of 2 mmAq (Example 1), a sample with the resistance-to-draw of 8 mmAq (Example 2), a sample with the resistance-to-draw of 15 mmAq (Example 3), a sample with the resistance-to-draw of 25 mmAq (Example 4), and a sample with the resistance-to-draw of 40 mmAq (Comparative Example 1). The resistance-to-draw of each sample was adjusted according to the length of the acetate filter.

Firstly, the ratio of subjects who answered that, of the direct inhalation and the puff inhalation, the direct inhalation was more natural was checked. The experiment result is as shown in FIG. 19. As shown in FIG. 19, in Comparative Example 1 (40 mmAq), the ratio of subjects who answered that the direct inhalation was more natural was 0%. Meanwhile, in Example 1 (2 mmAq), Example 2 (8 mmAq), Example 3 (15 mmAq), and Example 4 (25 mmAq), there were subjects who answered that the direct inhalation was more natural, and it was found that the ratio of subjects who answered that the direct inhalation was more natural became higher as the resistance-to-draw became smaller.

Secondly, the ratio of subjects who answered that the direct inhalation could not be performed upon attempting to perform the direct inhalation was checked. The experiment result is as shown in FIG. 20. As shown in FIG. 20, in Comparative Example 1 (40 mmAq), the ratio of subjects who answered that the direct inhalation could not be performed was 70%. Meanwhile, in Example 1 (2 mmAq), Example 2 (8 mmAq), Example 3 (15 mmAq), and Example 4 (25 mmAq), the ratio of subjects who answered that the direct inhalation could not be performed was 0%.

Thirdly, the degree of sense of resistance to be felt upon being attempted to perform the direct inhalation was checked with five-stage rating. The correspondence relation between the rating and the sense of resistance is as shown in FIG. 21, and the experiment result is as shown in FIG. 22. As shown in FIG. 22, in Comparative Example 1 (40 mmAq), all subjects rated that the sense of resistance was very strong (rating 5). Meanwhile, in Example 1 (2 mmAq), Example 2 (8 mmAq), Example 3 (15 mmAq), and Example 4 (25 mmAq), it was found that the sense of resistance became weaker as the resistance-to-draw became smaller. Particularly, in Example 1 (2 mmAq), subjects who answered that the sense of resistance was adequate (rating 3) accounted for 50%, and the remaining 50% answered relatively weak (rating 2) or weak (rating 1). Meanwhile, in Example 2 (8 mmAq), subjects who answered that the sense of resistance was adequate (rating 3) accounted for 50%, and the remaining 50% answered relatively strong (rating 4), and there were no subjects who answered relatively weak (rating 2) or very weak (rating 1).

From these experiment results, firstly, it was found that if the resistance-to-draw was 40 mmAq or more, 70% of the subjects answered that the direct inhalation could not be performed, whereas if the resistance-to-draw was 25 mmAq or less, there were no subjects who answered that the direct inhalation could not be performed (see FIG. 20). Secondly, it was found that if the resistance-to-draw was 15 mmAq or less, the ratio of subjects who answered that the direct inhalation was more natural was 50% or more (see FIG. 19). Thirdly, it was found that if the resistance-to-draw was 2 mmAq or more and 8 mmAq or less, subjects who answered that the sense of resistance was adequate (rating 3) was 50%, and if the resistance-to-draw was 2 mmAq, there were subjects who answered relatively weak (rating 2) or weak (rating 1), whereas if the resistance-to-draw was 8 mmAq, there were no subjects who answered relatively weak (rating 2) or weak (rating 1).

That is, it was found that the resistance-to-draw of the entire air flow path was preferably 25 mmAq or less. Furthermore, it was found that the resistance-to-draw of the entire air flow path was more preferably 15 mmAq or less. In addition, it was found that the resistance-to-draw of the entire air flow path was further preferably 2 mmAq or more and 8 mmAq or less.

INDUSTRIAL APPLICABILITY

According to the embodiment, it is possible to provide a flavor inhaler by which the deterioration of the inhaling flavor can be controlled by reducing the aerosol loss.

The invention claimed is:

1. A flavor inhaler comprising:
a housing having an air flow path continuous from an inlet to an outlet;
an atomizer configured to atomize an aerosol source without burning the aerosol source;
a switch for supplying a power source output to the atomizer during a period a user performs an inhaling action while not supplying the power source output to the atomizer during a period the user does not perform the inhaling action;
a sensor configured to output a response value that changes in accordance with the inhaling action of the user,
wherein at least a part of the air flow path includes an aerosol flow path which is a flow path of an aerosol generated from the atomizer,
wherein a resistance-to-draw of the entire air flow path is 25 mmAq or less,
wherein the resistance-to-draw of the entire air flow path is defined as pressure loss at a time of performing inhalation at 1050 mL/min by a vacuum pump at a state that the flavor inhaler is connected to the vacuum pump,
wherein the switch operates based on the response value output from the sensor,
wherein the housing has a first hollow provided at a side same with the inlet and the outlet relative to the sensor, and a second hollow provided at an opposite side of the inlet and the outlet relative to the sensor, and
wherein the first hollow and the second hollow are partitioned not to communicate with each other within the housing.

2. The flavor inhaler according to claim 1, wherein the housing includes a first housing that houses the atomizer, and a second housing, removable from the first housing, that houses a power source configured to accumulate power supplied to the atomizer, and
wherein the sensor is housed in the second housing and provided on a side of the first housing relative to the power source.

3. The flavor inhaler according to claim 2, wherein the inlet is provided between the sensor and the atomizer.

4. The flavor inhaler according to claim 1, wherein an end threshold value to be compared with the response value to determine whether to operate the switch not to supply the power source output to the atomizer is larger than a start threshold value to be compared with the response value to determine whether to operate the switch to supply the power source output to the atomizer.

5. The flavor inhaler according to claim 1, wherein the resistance-to-draw of the entire air flow path is 15 mmAq or less.

6. The flavor inhaler according to claim 1, wherein the resistance-to-draw of the entire air flow path is 2 mmAq or more and 8 mmAq or less.

7. The flavor inhaler according to claim 1, wherein the flavor inhaler is configured to allow the resistance-to-draw of the entire air flow path to be changeable to 25 mmAq or less.

8. A flavor inhaler comprising:
a housing having an air flow path continuous from an inlet to an outlet and
an atomizer configured to atomize an aerosol source without burning the aerosol source,
wherein at least a part of the air flow path includes an aerosol flow path which is a flow path of an aerosol generated from the atomizer, wherein a resistance-to-draw of the entire air flow path is 25 mmAq or less,
wherein the resistance-to-draw of the entire air flow path is defined as pressure loss at a time of performing inhalation at 1050 mL/min by a vacuum pump at a state that the flavor inhaler is connected to the vacuum pump,
wherein the air flow path includes a first air flow path passing through the atomizer and a second air flow path not passing through the atomizer,
wherein the inlet includes a first inlet configured to lead an air into the first air flow path and a second inlet configured to lead an air into the second air flow path,
wherein the outlet includes a first outlet configured to lead an air out from the first air flow path and a second outlet configured to lead an air out from the second air flow path,
wherein the second inlet is different from the first inlet, and
wherein the second inlet is communicable with the aerosol flow path at a side of the first outlet relative to the atomizer or communicates with the second outlet without communicating with the aerosol flow path.

9. The flavor inhaler according to claim 8, wherein an amount of air flowing in from the second inlet is 50% or more of a total amount of the amount of air flowing out from the first outlet and the amount of air flowing out from the second outlet.

10. The flavor inhaler according to claim 8, wherein the housing includes an inhaler housing that houses at least the atomizer, and a cartridge housing that houses at least a flavor source provided on a side of the first outlet relative to the atomizer,
wherein the inhaler housing has the second inlet communicable with the aerosol flow path at a side of the first outlet relative to the atomizer, and
wherein the cartridge housing forms at least a part of the second air flow path.

11. The flavor inhaler according to claim 10, wherein the cartridge housing is configured to be inserted into the inhaler housing along a predetermined direction,
wherein the cartridge housing has a first recess portion formed on an outside surface adjacent to the inhaler housing, and
wherein the first recess portion is annularly continued in a cross section perpendicular to the predetermined direction at a position corresponding to the second inlet in the predetermined direction, and forms a part of the second air flow path.

12. The flavor inhaler according to claim 8, wherein the housing includes an inhaler housing that houses at least the atomizer, and a cartridge housing that houses at least a flavor source provided on a side of the first outlet relative to the atomizer, and
wherein the inhaler housing has the second inlet communicating with the second outlet without communicating with the aerosol flow path.

13. The flavor inhaler according to claim 12, wherein the cartridge housing is configured to be inserted into the inhaler housing along a predetermined direction,
wherein the cartridge housing has a second recess portion formed on an outside surface adjacent to the inhaler housing, and
wherein the second recess portion is annularly continued in a cross section perpendicular to the predetermined direction at a position corresponding to the second inlet in the predetermined direction.

14. The flavor inhaler according to claim 8, wherein the housing includes an inhaler housing that houses at least the atomizer, and a cartridge housing that houses at least a flavor source provided on a side of the first outlet relative to the atomizer, and
wherein the second inlet is provided at a cartridge protruding portion if the cartridge housing includes the cartridge protruding portion extending toward a side of the first outlet from the inhaler housing in a predetermined direction, or the second inlet is provided at an inhaler protruding portion if the inhaler housing includes the inhaler protruding portion extending toward the side of the first outlet from the cartridge housing in the predetermined direction.

15. The flavor inhaler according to claim 8, further comprising:
a flavor source provided on a side of the first outlet relative to the atomizer, wherein
the second inlet is provided on a side of the second outlet relative to the flavor source.

16. A flavor inhaler comprising:
a housing having an air flow path continuous from an inlet to an outlet an atomizer configured to atomize an aerosol source without burning the aerosol source;
a flavor source provided on a side of the outlet relative to the atomizer,
wherein at least a part of the air flow path includes an aerosol flow path which is a flow path of an aerosol generated from the atomizer,
wherein a resistance-to-draw of the entire air flow path is 25 mmAq or less,
wherein the resistance-to-draw of the entire air flow path is defined as pressure loss at a time of performing inhalation at 1050 mL/min by a vacuum pump at a state that the flavor inhaler is connected to the vacuum pump,
wherein the aerosol flow path includes a first aerosol flow path configured to lead an aerosol toward a side of the outlet through the flavor source, and a second aerosol flow path different from the first aerosol flow path, and
wherein a reduction ratio of aerosol in the second aerosol flow path is smaller than a reduction ratio of aerosol in the first aerosol flow path.

17. The flavor inhaler according to claim 16, wherein the second aerosol flow path is a flow path configured to lead an aerosol toward a side of the outlet without passing through the flavor source.

18. A flavor inhaler comprising:
a housing having an air flow path continuous from an inlet to an outlet
an atomizer configured to atomize an aerosol source without burning the aerosol source;
a flavor source unit having a flavor source provided on a side of the outlet relative to the atomizer,
wherein at least a part of the air flow path includes an aerosol flow path which is a flow path of an aerosol generated from the atomizer,
wherein a resistance-to-draw of the entire air flow path is 25 mmAq or less,
wherein the resistance-to-draw of the entire air flow path is defined as pressure loss at a time of performing inhalation at 1050 mL/min by a vacuum pump at a state that the flavor inhaler is connected to the vacuum pump,
wherein the housing has a shape extending along a predetermined direction,
wherein the flavor source unit is arranged in the housing to partition the aerosol flow path into a first space at the inlet side and a second space at the outlet, and
wherein an area of the flavor source unit being exposed to at least any one of the first space and the second space is larger than a cross section area defined by an inner circumference of the housing in a cross section perpendicular to the predetermined direction.

19. The flavor inhaler according to claim 18, wherein the flavor source unit partitions the first space and the second space along the predetermined direction,
wherein the flavor source unit has a first wall body being exposed to the first space and the second space, and a second wall body continuing to the first wall body,
wherein the first wall body is formed by a member having air permeability, and
wherein an area of an outer surface of the first wall body is larger than an area of an outer surface of the second wall body.

* * * * *